US009974929B2

(12) United States Patent
Ciccone et al.

(10) Patent No.: US 9,974,929 B2
(45) Date of Patent: May 22, 2018

(54) ANCHORING SYSTEM FOR A MEDICAL ARTICLE

(71) Applicant: Venetec International, Inc., Covington, GA (US)

(72) Inventors: Paul Ciccone, Social Circle, GA (US); Gary Peters, Peachtree City, GA (US); Cory McCluskey, Encinitas, CA (US)

(73) Assignee: Venetec International, Inc., Murray Hill, NJ (US)

( * ) Notice: Subject to any disclaimer, the term of this patent is extended or adjusted under 35 U.S.C. 154(b) by 0 days. days.

(21) Appl. No.: 15/336,537

(22) Filed: Oct. 27, 2016

(65) Prior Publication Data

US 2017/0043131 A1    Feb. 16, 2017

Related U.S. Application Data

(63) Continuation of application No. 13/001,924, filed as application No. PCT/US2008/068854 on Jun. 30, 2008, now Pat. No. 9,480,821.

(51) Int. Cl.
*A61M 25/02*    (2006.01)
*A61M 25/00*    (2006.01)

(52) U.S. Cl.
CPC ........ *A61M 25/02* (2013.01); *A61M 25/0017* (2013.01); *A61M 2025/0246* (2013.01);
(Continued)

(58) Field of Classification Search
CPC .............. A61M 25/02; A61M 25/0017; A61M 2025/024; A61M 2025/0246; A61M 2025/0266; A61M 2025/028
See application file for complete search history.

(56) References Cited

U.S. PATENT DOCUMENTS 2,525,398 A    10/1950 Collins
2,533,961 A    12/1950 Rousseau et al.
(Continued)

FOREIGN PATENT DOCUMENTS

CA    995995 A1    8/1976
CA    2281457 A1    2/2001
(Continued)

OTHER PUBLICATIONS

U.S. Appl. No. 13/500,853, filed Jul. 13, 2012 Examiner's Answer to Appeal Brief dated Dec. 20, 2016.
(Continued)

*Primary Examiner* — Kami A Bosworth
(74) *Attorney, Agent, or Firm* — Rutan & Tucker, LLP

(57) ABSTRACT

An anchoring system for securing a catheter to a patient includes an anchor pad and a retainer. The retainer is supported by the anchor pad and may include a base and a cover. A groove upon the base can be arranged to receive a branching site of a catheter where the lumens merge distal to the insertion site. One or more posts may also protrude from the base to the cover at a position disposed between the two distal branches of the catheter. The cover closes over the base securing the branching site between the groove and the posts. The contact between the retainer and catheter thereby inhibits inadvertent motion of the catheter upon the patient. A latch mechanism may be disposed upon the retainer to maintain the cover in a closed position over the branching site of the catheter on the base.

15 Claims, 24 Drawing Sheets

(52) U.S. Cl.
CPC ............... *A61M 2025/0266* (2013.01); *A61M 2205/583* (2013.01)

(56) References Cited

U.S. PATENT DOCUMENTS

| | | |
|---|---|---|
| 2,707,953 A | 5/1955 | Ryan |
| 2,893,671 A | 7/1959 | Flora et al. |
| 3,059,645 A | 10/1962 | Hasbrouck et al. |
| 3,064,648 A | 11/1962 | Bujan |
| 3,167,072 A | 1/1965 | Stone et al. |
| 3,482,569 A | 12/1969 | Raaelli, Sr. |
| 3,529,597 A | 9/1970 | Fuzak |
| 3,602,227 A | 8/1971 | Andrew |
| 3,630,195 A | 12/1971 | Santomieri |
| 3,677,250 A | 7/1972 | Thomas |
| 3,766,915 A | 10/1973 | Rychlik |
| 3,834,380 A | 9/1974 | Boyd |
| 3,847,370 A | 11/1974 | Engelsher |
| 3,856,020 A | 12/1974 | Kovac |
| 3,896,527 A | 7/1975 | Miller et al. |
| 3,900,026 A | 8/1975 | Wagner |
| 3,905,322 A | 9/1975 | Peterman et al. |
| 3,906,592 A | 9/1975 | Sakasegawa et al. |
| 3,906,946 A | 9/1975 | Nordstrom |
| 3,934,576 A | 1/1976 | Danielsson |
| 3,942,228 A | 3/1976 | Buckman et al. |
| 3,973,565 A | 8/1976 | Steer |
| 3,993,081 A | 11/1976 | Cussell |
| 4,020,835 A | 5/1977 | Nordstrom et al. |
| 4,030,540 A | 6/1977 | Roma |
| 4,057,066 A | 11/1977 | Taylor |
| 4,059,105 A | 11/1977 | Cutruzzula et al. |
| 4,082,094 A | 4/1978 | Dailey |
| 4,114,618 A | 9/1978 | Vargas |
| 4,129,128 A | 12/1978 | McFarlane |
| 4,133,307 A | 1/1979 | Ness |
| 4,142,527 A | 3/1979 | Garcia |
| 4,149,539 A | 4/1979 | Cianci |
| 4,161,177 A | 7/1979 | Fuchs |
| 4,170,995 A | 10/1979 | Levine et al. |
| 4,193,174 A | 3/1980 | Stephens |
| 4,209,015 A | 6/1980 | Wicks |
| 4,224,937 A | 9/1980 | Gordon |
| 4,248,229 A | 2/1981 | Miller |
| 4,250,880 A | 2/1981 | Gordon |
| 4,316,461 A | 2/1982 | Marais et al. |
| 4,324,236 A | 4/1982 | Gordon et al. |
| 4,326,519 A | 4/1982 | D'Alo et al. |
| 4,333,468 A | 6/1982 | Geist |
| 4,356,599 A | 11/1982 | Larson et al. |
| 4,362,156 A | 12/1982 | Feller, Jr. et al. |
| 4,392,853 A | 7/1983 | Muto |
| 4,397,647 A | 8/1983 | Gordon |
| 4,402,691 A | 9/1983 | Rosenthal et al. |
| 4,405,163 A | 9/1983 | Voges et al. |
| 4,405,312 A | 9/1983 | Gross et al. |
| 4,442,994 A | 4/1984 | Logsdon |
| 4,449,975 A | 5/1984 | Perry |
| 4,453,933 A | 6/1984 | Speaker |
| 4,474,559 A | 10/1984 | Steiger |
| 4,480,639 A | 11/1984 | Peterson et al. |
| 4,484,913 A | 11/1984 | Swauger |
| 4,498,903 A | 2/1985 | Mathew |
| 4,516,968 A | 5/1985 | Marshall et al. |
| 4,517,971 A | 5/1985 | Sorbonne |
| 4,563,177 A | 1/1986 | Kamen |
| 4,583,976 A | 4/1986 | Ferguson |
| 4,623,102 A | 11/1986 | Hough, Jr. |
| 4,633,863 A | 1/1987 | Filips et al. |
| 4,650,473 A | 3/1987 | Bartholomew et al. |
| 4,659,329 A | 4/1987 | Annis |
| 4,660,555 A | 4/1987 | Payton |
| 4,711,636 A | 12/1987 | Bierman |
| 4,726,716 A | 2/1988 | McGuire |
| 4,733,666 A | 3/1988 | Mercer, Jr. |
| 4,742,824 A | 5/1988 | Payton et al. |
| 4,762,513 A | 8/1988 | Choy et al. |
| 4,775,121 A | 10/1988 | Carty |
| 4,808,162 A | 2/1989 | Oliver |
| 4,823,789 A | 4/1989 | Beisang, III |
| 4,826,466 A | 5/1989 | Triquet |
| 4,826,486 A | 5/1989 | Palsrok et al. |
| 4,838,878 A | 6/1989 | Kalt et al. |
| 4,852,844 A | 8/1989 | Villaveces |
| 4,857,058 A | 8/1989 | Payton |
| 4,863,432 A | 9/1989 | Kvalo |
| 4,869,465 A | 9/1989 | Yirmiyahu et al. |
| 4,880,412 A | 11/1989 | Weiss |
| 4,896,465 A | 1/1990 | Rhodes et al. |
| 4,897,082 A | 1/1990 | Erskine |
| 4,898,587 A | 2/1990 | Mera |
| 4,919,654 A | 4/1990 | Kalt |
| 4,932,943 A | 6/1990 | Nowak |
| 4,944,728 A | 7/1990 | Carrell et al. |
| 4,952,207 A | 8/1990 | Lemieux |
| 4,955,864 A | 9/1990 | Hajduch |
| 4,976,700 A | 12/1990 | Tollini |
| 4,981,475 A | 1/1991 | Haindl |
| 4,997,421 A | 3/1991 | Palsrok et al. |
| 5,000,741 A | 3/1991 | Kalt |
| 5,037,397 A | 8/1991 | Kalt et al. |
| 5,073,166 A | 12/1991 | Parks et al. |
| 5,073,170 A | 12/1991 | Schneider |
| 5,084,026 A | 1/1992 | Shapiro |
| 5,098,399 A | 3/1992 | Tollini |
| 5,100,393 A | 3/1992 | Johnson |
| 5,112,313 A | 5/1992 | Sallee |
| 5,137,519 A | 8/1992 | Littrell et al. |
| 5,147,322 A | 9/1992 | Bowen et al. |
| 5,156,641 A | 10/1992 | White |
| 5,188,609 A | 2/1993 | Bayless et al. |
| 5,192,273 A | 3/1993 | Bierman |
| 5,192,274 A | 3/1993 | Bierman |
| 5,195,981 A | 3/1993 | Johnson |
| 5,210,913 A | 5/1993 | Clark |
| 5,226,892 A | 7/1993 | Boswell |
| 5,234,185 A | 8/1993 | Hoffman et al. |
| 5,248,306 A | 9/1993 | Clark et al. |
| 5,263,943 A | 11/1993 | Vanderbrook |
| 5,266,401 A | 11/1993 | Tollini |
| 5,267,967 A | 12/1993 | Schneider |
| 5,282,463 A | 2/1994 | Hammersley |
| 5,292,312 A | 3/1994 | Delk et al. |
| 5,304,146 A | 4/1994 | Johnson et al. |
| 5,306,243 A | 4/1994 | Bonaldo |
| 5,306,256 A | 4/1994 | Jose |
| 5,308,337 A | 5/1994 | Bingisser |
| 5,314,411 A | 5/1994 | Bierman et al. |
| 5,322,514 A | 6/1994 | Steube et al. |
| 5,330,438 A | 7/1994 | Gollobin et al. |
| 5,334,186 A | 8/1994 | Alexander |
| 5,336,195 A | 8/1994 | Daneshvar |
| 5,338,308 A | 8/1994 | Wilk |
| 5,342,317 A | 8/1994 | Claywell |
| 5,344,406 A | 9/1994 | Spooner |
| 5,344,414 A | 9/1994 | Lopez et al. |
| 5,346,479 A | 9/1994 | Schneider |
| 5,352,211 A | 10/1994 | Merskelly |
| 5,354,282 A | 10/1994 | Bierman |
| 5,354,283 A | 10/1994 | Bark et al. |
| 5,368,575 A | 11/1994 | Chang |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,389,082 A | 2/1995 | Baugues et al. |
| 5,395,344 A | 3/1995 | Beisang, III et al. |
| 5,398,679 A | 3/1995 | Freed |
| 5,403,285 A | 4/1995 | Roberts |
| 5,413,562 A | 5/1995 | Swauger |
| 5,431,695 A | 7/1995 | Wiklund et al. |
| 5,443,460 A | 8/1995 | Miklusek |
| 5,449,349 A | 9/1995 | Sallee et al. |

(56) References Cited

U.S. PATENT DOCUMENTS

| | | |
|---|---|---|
| 5,456,671 A | 10/1995 | Bierman |
| 5,468,228 A | 11/1995 | Gebert |
| 5,468,230 A | 11/1995 | Corn |
| 5,468,231 A | 11/1995 | Newman et al. |
| 5,470,321 A | 11/1995 | Forster et al. |
| D364,922 S | 12/1995 | Bierman |
| 5,484,420 A | 1/1996 | Russo |
| 5,494,245 A | 2/1996 | Suzuki et al. |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,522,803 A | 6/1996 | Teissen-Simony |
| 5,527,293 A | 6/1996 | Zamierowski |
| 5,531,695 A | 7/1996 | Swisher |
| 5,549,567 A | 8/1996 | Wolman |
| D375,355 S | 11/1996 | Bierman |
| 5,578,013 A | 11/1996 | Bierman |
| 5,626,565 A | 5/1997 | Landis et al. |
| 5,632,274 A | 5/1997 | Quedens et al. |
| 5,637,098 A | 6/1997 | Bierman |
| 5,638,814 A | 6/1997 | Byrd |
| 5,643,217 A | 7/1997 | Dobkin |
| 5,672,159 A | 9/1997 | Warrick |
| 5,681,290 A | 10/1997 | Alexander |
| 5,685,859 A | 11/1997 | Kornerup |
| 5,686,096 A | 11/1997 | Khan et al. |
| 5,690,617 A | 11/1997 | Wright |
| 5,693,032 A | 12/1997 | Bierman |
| 5,697,907 A | 12/1997 | Gaba |
| 5,702,371 A | 12/1997 | Bierman |
| D389,911 S | 1/1998 | Bierman |
| 5,709,665 A | 1/1998 | Vergano et al. |
| 5,722,959 A | 3/1998 | Bierman |
| 5,738,660 A | 4/1998 | Luther |
| 5,755,225 A | 5/1998 | Hutson |
| 5,795,335 A | 8/1998 | Zinreich |
| 5,800,402 A | 9/1998 | Bierman |
| 5,810,781 A | 9/1998 | Bierman |
| 5,810,835 A | 9/1998 | Ryan et al. |
| 5,827,230 A | 10/1998 | Bierman |
| 5,827,239 A | 10/1998 | Dillon et al. |
| 5,833,667 A | 11/1998 | Bierman |
| 5,846,255 A | 12/1998 | Casey |
| 5,916,199 A | 6/1999 | Miles |
| 5,944,696 A | 8/1999 | Bayless et al. |
| 5,989,213 A | 11/1999 | Maginot |
| 6,001,081 A | 12/1999 | Collen et al. |
| 6,015,119 A | 1/2000 | Starchevich |
| 6,027,480 A | 2/2000 | Davis et al. |
| 6,074,368 A | 6/2000 | Wright |
| 6,113,577 A | 9/2000 | Hakky et al. |
| 6,132,398 A | 10/2000 | Bierman |
| 6,139,532 A | 10/2000 | Howell et al. |
| 6,206,897 B1 | 3/2001 | Jamiolkowski et al. |
| 6,213,979 B1 | 4/2001 | Bierman |
| 6,224,571 B1 | 5/2001 | Bierman |
| 6,228,064 B1 | 5/2001 | Abita et al. |
| 6,231,548 B1 | 5/2001 | Bassett |
| 6,273,873 B1 | 8/2001 | Fleischer |
| 6,283,945 B1 | 9/2001 | Bierman |
| 6,290,265 B1 | 9/2001 | Warburton-Pitt et al. |
| 6,290,676 B1 | 9/2001 | Bierman |
| 6,311,933 B1 | 11/2001 | Starchevich |
| 6,332,874 B1 | 12/2001 | Eliasen et al. |
| 6,361,523 B1 | 3/2002 | Bierman |
| 6,387,075 B1 | 5/2002 | Stivland et al. |
| 6,387,076 B1 | 5/2002 | Landuyt |
| 6,413,240 B1 | 7/2002 | Bierman et al. |
| 6,428,513 B1 | 8/2002 | Abrahamson |
| 6,428,514 B1 | 8/2002 | Goebel et al. |
| 6,428,516 B1 | 8/2002 | Bierman |
| 6,447,485 B2 | 9/2002 | Bierman |
| 6,447,486 B1 | 9/2002 | Tollini |
| 6,458,104 B2 | 10/2002 | Gautsche |
| 6,482,183 B1 | 11/2002 | Pausch et al. |
| 6,488,664 B1 | 12/2002 | Solomon et al. |
| 6,491,713 B1 | 12/2002 | Deininger et al. |
| 6,500,154 B1 | 12/2002 | Hakky et al. |
| 6,572,587 B2 | 6/2003 | Lerman et al. |
| 6,572,588 B1 | 6/2003 | Bierman et al. |
| 6,582,403 B1 | 6/2003 | Bierman et al. |
| 6,585,703 B1 | 7/2003 | Kassel et al. |
| 6,631,715 B2 | 10/2003 | Kim |
| 6,663,600 B2 | 12/2003 | Bierman et al. |
| 6,786,892 B2 | 9/2004 | Bierman |
| 6,824,527 B2 | 11/2004 | Gollobin |
| 6,837,875 B1 | 1/2005 | Bierman |
| 6,841,715 B2 | 1/2005 | Roberts |
| 6,872,194 B2 | 3/2005 | Doyle et al. |
| 6,929,625 B2 | 8/2005 | Bierman |
| 6,951,550 B2 | 10/2005 | Bierman |
| 6,972,003 B2 | 12/2005 | Bierman et al. |
| 6,979,320 B2 | 12/2005 | Bierman |
| 6,984,145 B1 | 1/2006 | Lim |
| 7,018,362 B2 | 3/2006 | Bierman et al. |
| 7,137,968 B1 | 11/2006 | Burrell et al. |
| D533,442 S | 12/2006 | Baylor |
| 7,175,615 B2 | 2/2007 | Hanly et al. |
| 7,247,150 B2 | 7/2007 | Bierman |
| 7,294,752 B1 | 11/2007 | Propp |
| D593,680 S | 6/2009 | Hafele et al. |
| 7,563,251 B2 | 7/2009 | Bierman et al. |
| 7,704,260 B2 | 4/2010 | Skakoon et al. |
| 7,776,003 B2 | 8/2010 | Zauner |
| 7,785,295 B2 | 8/2010 | Bierman |
| 8,016,792 B2 | 9/2011 | Wright et al. |
| 8,366,678 B2 | 2/2013 | Bierman et al. |
| 8,419,689 B2 | 4/2013 | Fink et al. |
| 8,728,039 B2 | 5/2014 | Bierman et al. |
| 9,138,560 B2 | 9/2015 | Wright et al. |
| 9,468,740 B2 | 10/2016 | Bierman et al. |
| 9,480,821 B2 | 11/2016 | Ciccone et al. |
| 2002/0068904 A1 | 6/2002 | Bierman et al. |
| 2002/0165493 A1 | 11/2002 | Bierman |
| 2003/0229313 A1 | 12/2003 | Bierman |
| 2004/0034330 A1 | 2/2004 | Bierman et al. |
| 2005/0096606 A1 | 5/2005 | Millerd |
| 2005/0113759 A1 | 5/2005 | Mueller et al. |
| 2005/0192539 A1 | 9/2005 | Bierman et al. |
| 2005/0197628 A1 | 9/2005 | Roberts et al. |
| 2006/0089600 A1 | 4/2006 | Bierman et al. |
| 2006/0129103 A1 | 6/2006 | Bierman et al. |
| 2006/0135944 A1 | 6/2006 | Bierman |
| 2007/0142782 A2 | 6/2007 | Bierman |
| 2007/0219500 A1 | 9/2007 | Wright et al. |
| 2007/0276335 A1 | 11/2007 | Bierman |
| 2008/0200880 A1 | 8/2008 | Kyvik et al. |
| 2009/0143740 A1 | 6/2009 | Bierman et al. |
| 2009/0143741 A1 | 6/2009 | Burn |
| 2009/0209906 A1 | 8/2009 | Tanaka et al. |
| 2010/0100049 A1 | 4/2010 | Godfrey |
| 2010/0324491 A1 | 12/2010 | Bierman et al. |
| 2012/0123343 A1 | 5/2012 | Aviles |
| 2012/0136314 A1 | 5/2012 | Ciccone et al. |
| 2012/0143140 A1 | 6/2012 | Bierman et al. |
| 2012/0271240 A1 | 10/2012 | Andino et al. |
| 2014/0343501 A1 | 11/2014 | Bierman et al. |

FOREIGN PATENT DOCUMENTS

| | | |
|---|---|---|
| CA | 2483995 A1 | 4/2004 |
| DE | 2341297 A1 | 4/1975 |
| EP | 0064284 A2 | 11/1982 |
| EP | 0247590 A2 | 12/1987 |
| EP | 0356683 A1 | 3/1990 |
| EP | 0440101 A2 | 8/1991 |
| EP | 0567029 A1 | 10/1993 |
| EP | 0931560 A1 | 7/1999 |
| FR | 1184139 A | 7/1959 |
| FR | 2381529 A1 | 9/1978 |
| FR | 2852520 A1 | 9/2004 |
| GB | 2063679 A | 6/1981 |
| GB | 2086466 A | 5/1982 |

(56) References Cited

FOREIGN PATENT DOCUMENTS

| | | |
|---|---|---|
| GB | 2288542 A | 10/1995 |
| GB | 2333234 A | 7/1999 |
| GB | 2344054 A | 5/2000 |
| JP | S60-051377 | 4/1985 |
| JP | 01308572 | 12/1989 |
| JP | H04-037448 | 3/1992 |
| JP | 1994-344852 A | 12/1994 |
| JP | 1995-028563 | 5/1995 |
| JP | H08-257138 A | 10/1996 |
| JP | 2005-535432 A | 11/2005 |
| JP | 04-051767 B2 | 2/2008 |
| JP | 2009-507533 A | 2/2009 |
| WO | 8001458 A1 | 7/1980 |
| WO | 8502774 A1 | 7/1985 |
| WO | 9116939 A1 | 11/1991 |
| WO | 9219309 A1 | 11/1992 |
| WO | 9610435 A1 | 4/1996 |
| WO | 1996/026756 A1 | 9/1996 |
| WO | 9853872 A1 | 12/1998 |
| WO | 9902399 A1 | 1/1999 |
| WO | 9955409 A1 | 11/1999 |
| WO | 2004016309 A2 | 2/2004 |
| WO | 2006/113620 A2 | 10/2006 |
| WO | 2007028007 A2 | 3/2007 |
| WO | 2011/060197 A1 | 5/2011 |

OTHER PUBLICATIONS

EP 14770518.0 filed Sep. 7, 2015 Extended European Search Report, dated Aug. 23, 2016.
Extended European Search Report for EP 07 71 7867, PCT/US2007/000969, dated Oct. 14, 2010.
Medtronic. Intracranial Pressure Monitoring: A Handbook for the Nursing Professional. (2000).
Multiple-Lumen Central Venous Catheterization Product With ARROW+gard.TM. Antiseptic Surface (Arrow International brochure) (Apr. 1994).
PCT/US07/00969 filed Jan. 11, 2007, International Search Report and Written Opinion, dated Sep. 25, 2007.
PCT/US07/00969 filed Nov. 1, 2007 International Search Report dated Sep. 25, 2007.
PCT/US07/00969 filed Nov. 1, 2007 Written Opinion dated Sep. 25, 2007.
PCT/US07/84346 filed Nov. 9, 2007 International Search Report and Written Opinion dated Oct. 31, 2008.
PCT/US08/68854 filed Jun. 30, 2008 International Search Report dated Sep. 3, 2008.
PCT/US08/68854 filed Jun. 30, 2008 Written Opinion dated Sep. 5, 2008.
PCT/US10/56421 filed Nov. 11, 2010 International Search Report and Written Opinion dated Jan. 12, 2011.
PCT/US2001/006836 filed Feb. 3, 2001 International Search Report dated Aug. 2, 2001.
PCT/US2008/068854 filed Jun. 30, 2008 International Preliminary Report dated Sep. 5, 2008.
PCT/US2014/020207 filed Mar. 4, 2014 International Search Report and Written Opinion dated Jun. 12, 2014.
Photographs (4) of Catheter Clamp and Rigid Fastener sold by Arrow International. Inc. (2009).
Search Result, Percufix® Catheter Cuff Kit, downloaded from the Internet on Aug. 15, 2001.
U.S. Appl. No. 11/690,101, filed Mar. 22, 2007 Advisory Action dated Dec. 3, 2014.
U.S. Appl. No. 11/690,101, filed Mar. 22, 2007 Final Office Action dated Sep. 25, 2014.
U.S. Appl. No. 13/001,924, filed Jan. 30, 2012 Advisory Action dated Jun. 25, 2015.
U.S. Appl. No. 13/001,924, filed Jan. 30, 2012 Non-Final Office Action dated Mar. 28, 2016.
U.S. Appl. No. 13/500,853, filed Jul. 13, 2012 Final Office Action dated Apr. 12, 2016.
U.S. Appl. No. 13/500,853, filed Jul. 13, 2012 Non-Final Office Action dated Aug. 21, 2014.
U.S. Appl. No. 13/500,853, filed Jul. 13, 2012 Non-Final Office Action dated Oct. 7, 2015.
U.S. Appl. No. 14/283,137, filed May 20, 2014 Advisoary Action dated May 17, 2016.
U.S. Appl. No. 14/283,137, filed May 20, 2014 Final Office Action dated Mar. 3, 2016.
U.S. Appl. No. 14/283,137, filed May 20, 2014 Non-Final Office Action dated Oct. 22, 2015.
U.S. Appl. No. 14/859,090, filed Sep. 18, 2015 Non-Final Office Action dated Apr. 7, 2016.
U.S. Appl. No. 14/859,090, filed Sep. 18, 2015 Noticeof Allowance dated Sep. 27, 2016.
EP 14770518.0 filed Sep. 7, 2015 Office Action, dated Nov. 20, 2017.
JP 2016-500588 filed Sep. 11, 2015 Office Action dated Dec. 27, 2017.
U.S. Appl. No. 14/764,979, filed Jul. 30, 2015 Non-Final Office Action dated Feb. 7, 2018.

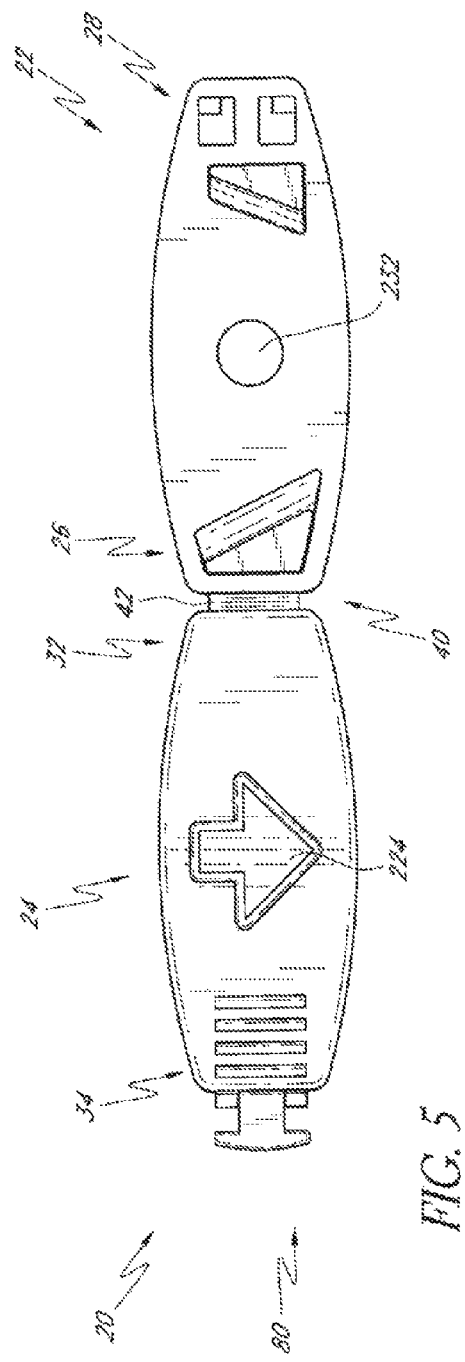
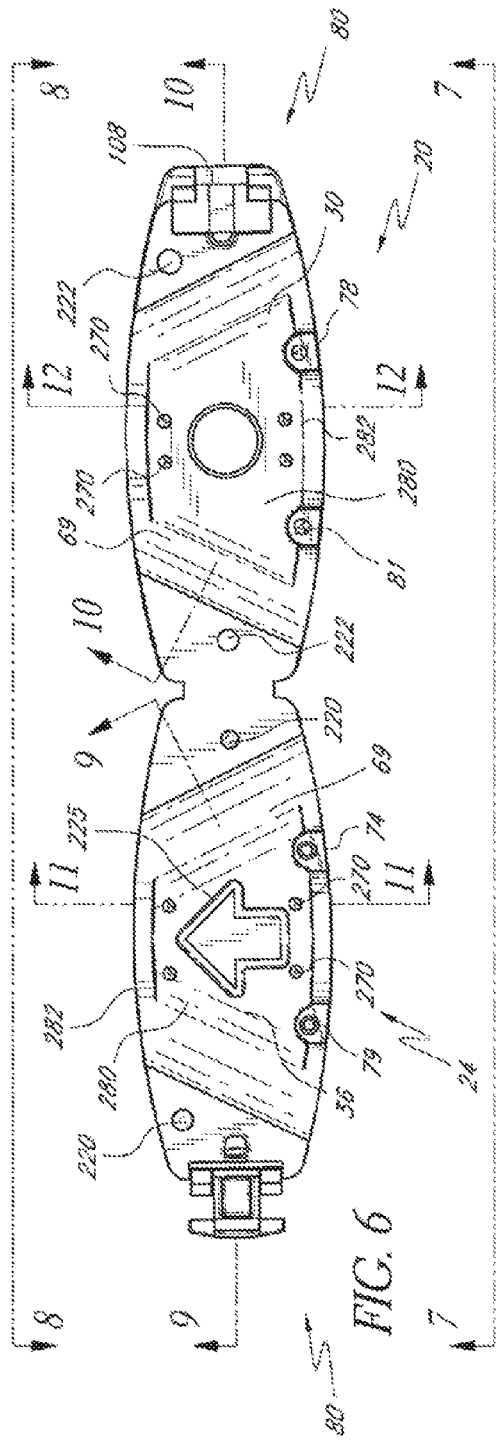
FIG. 5
FIG. 6

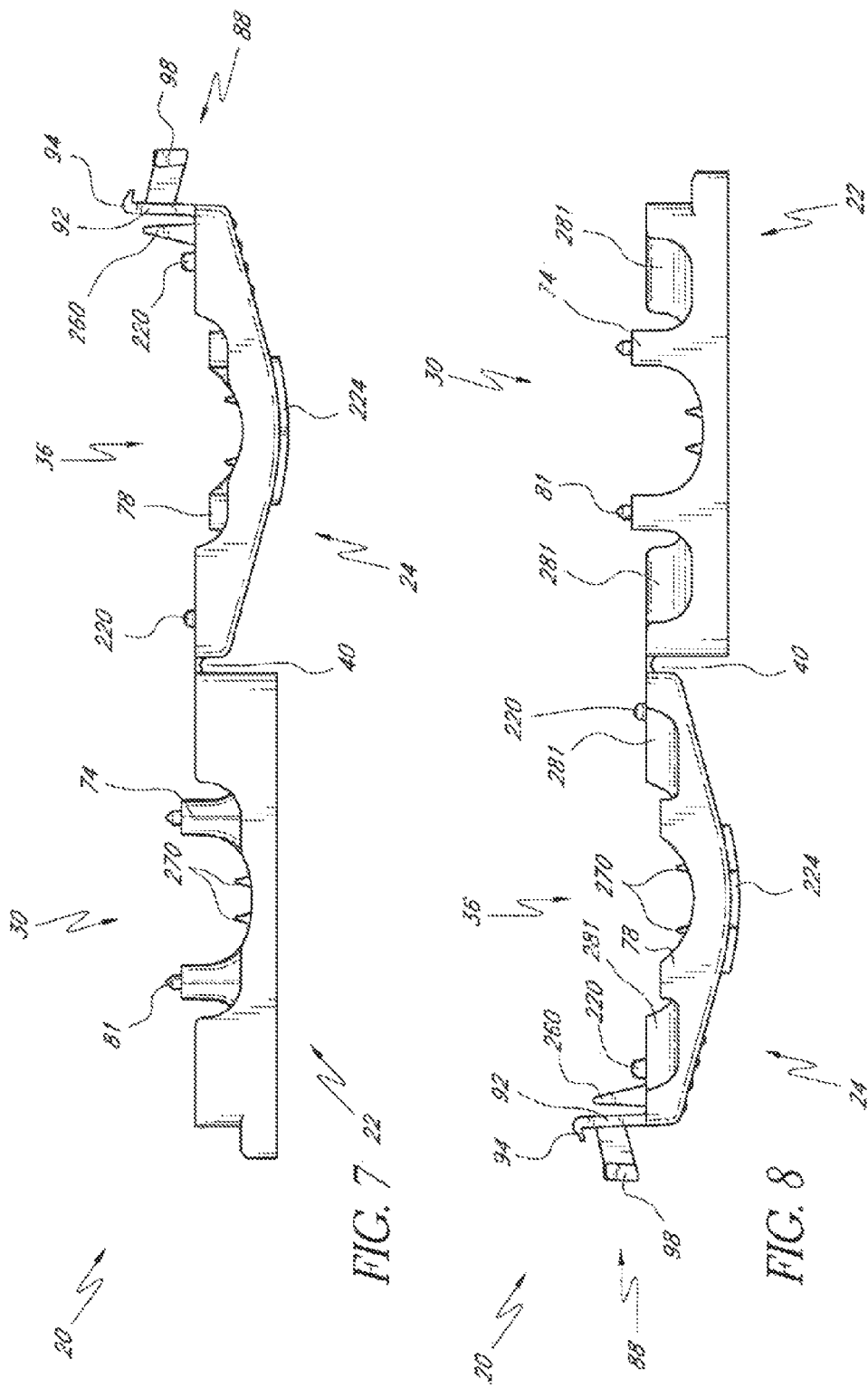

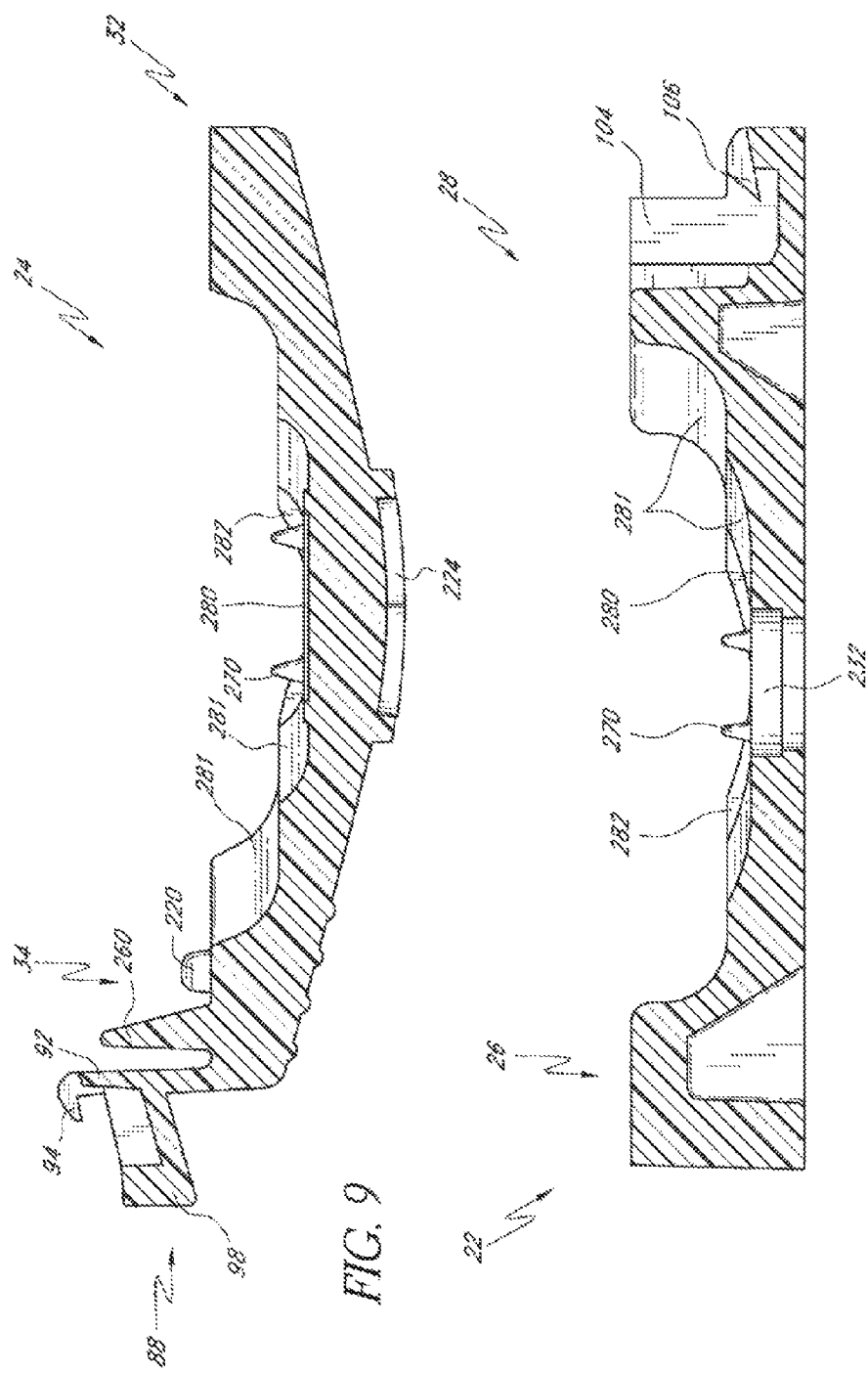

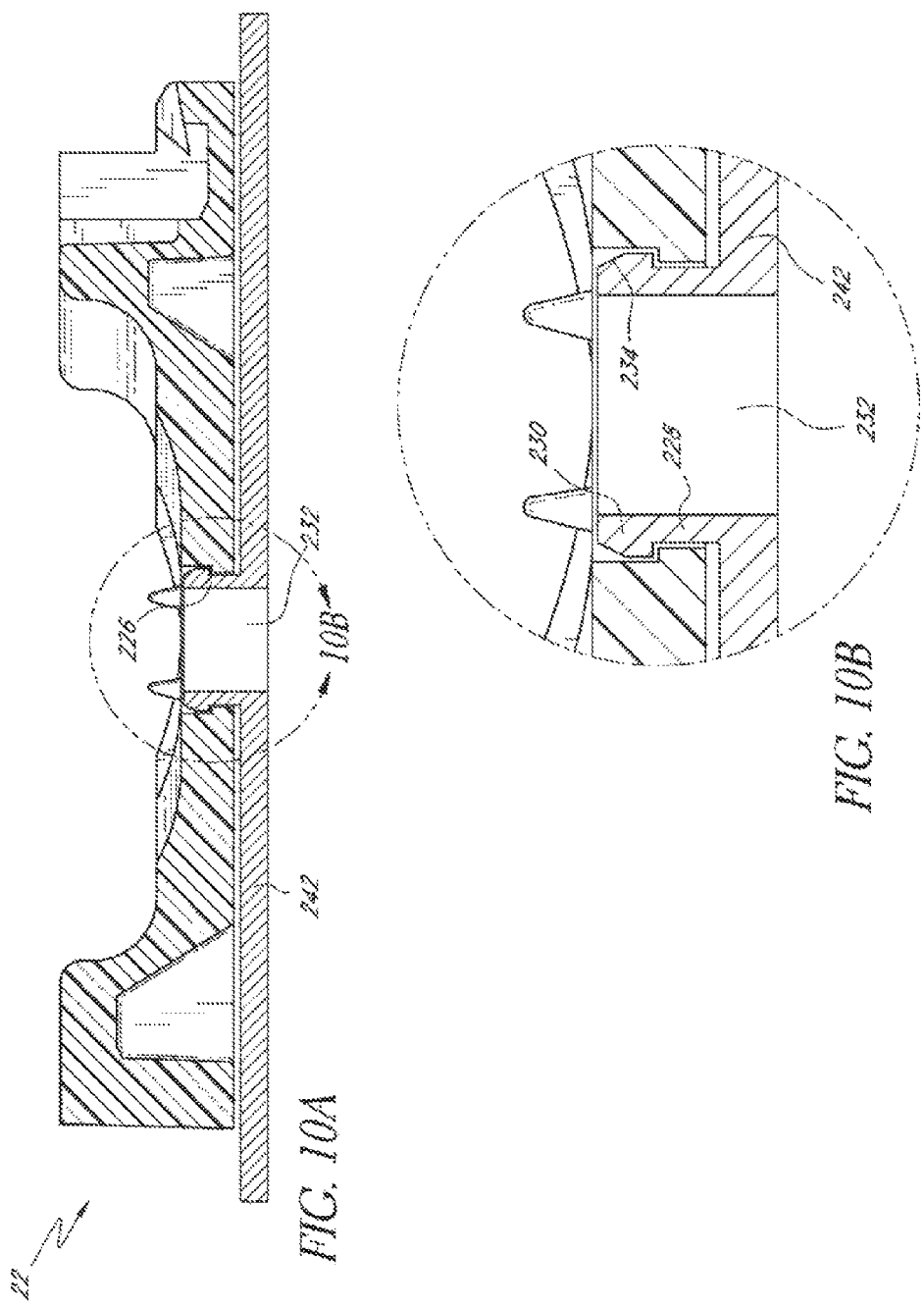

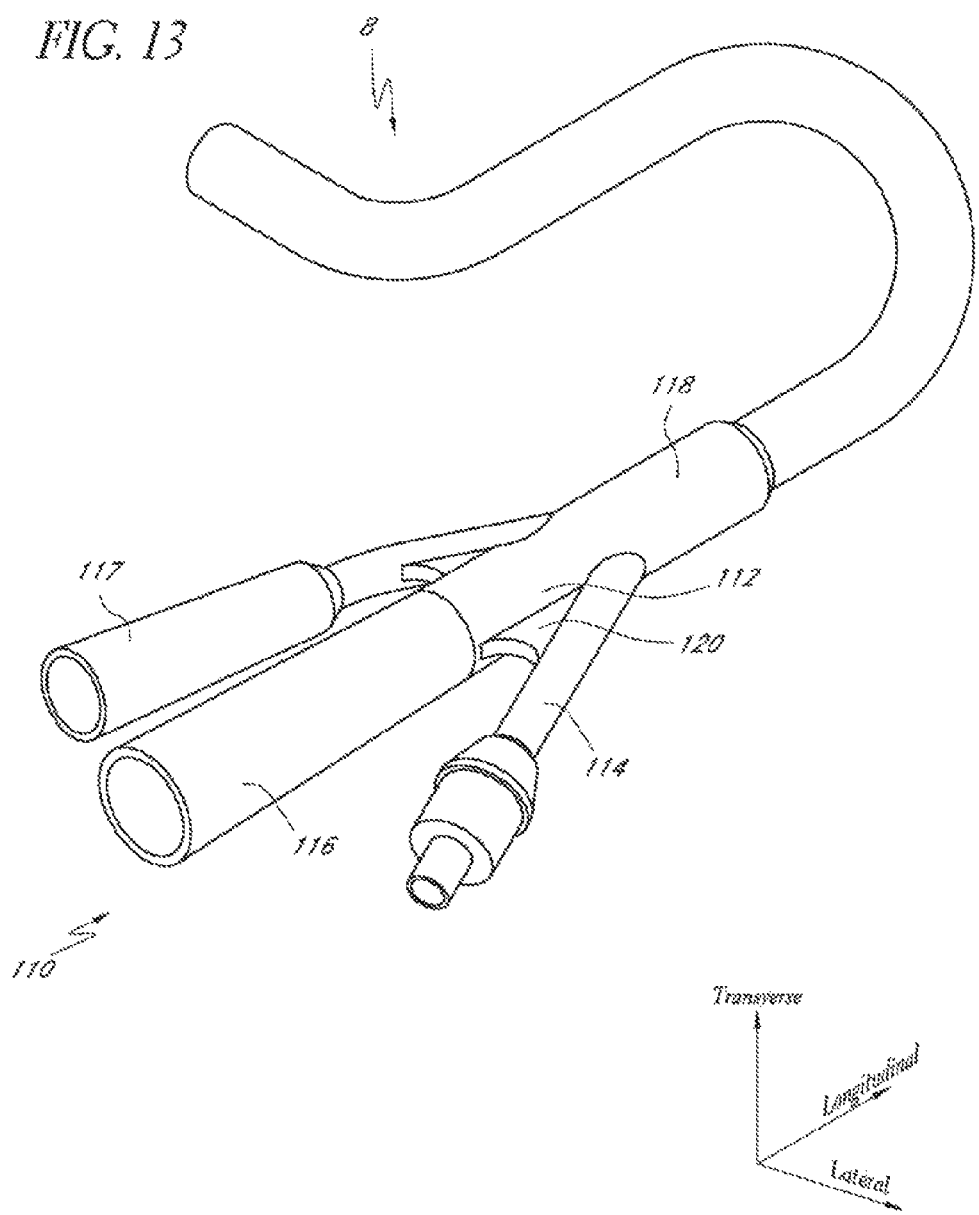

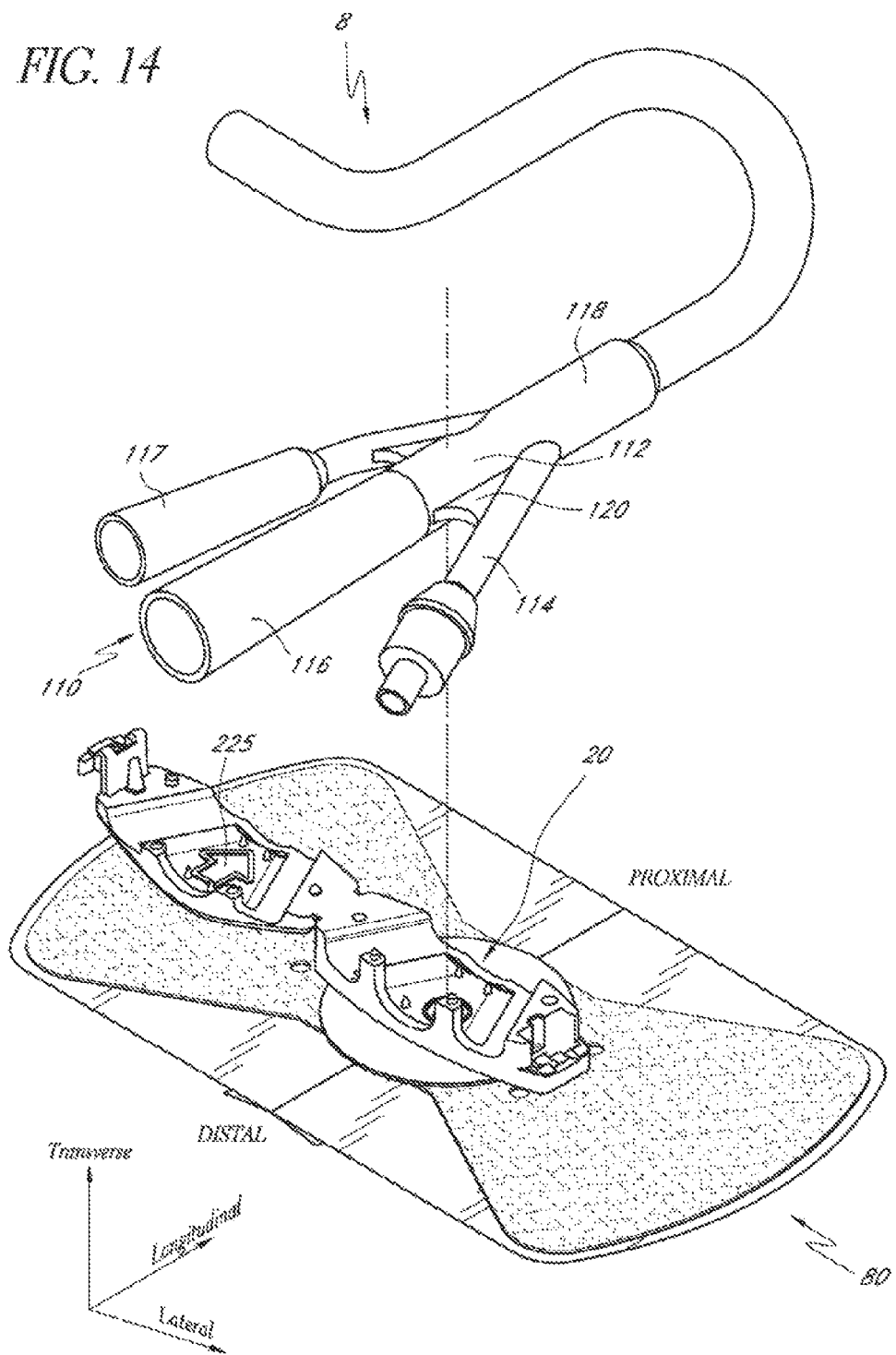

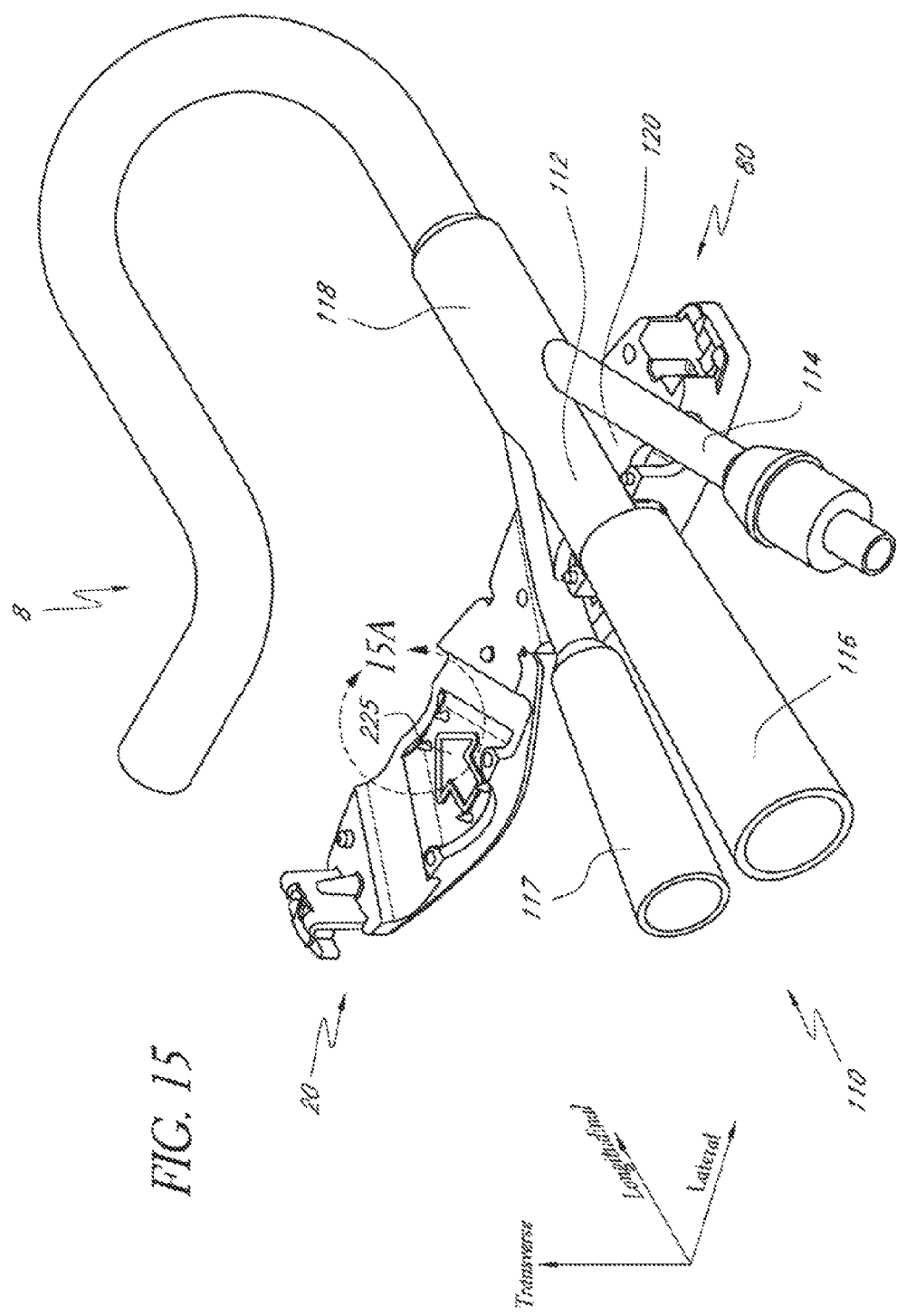

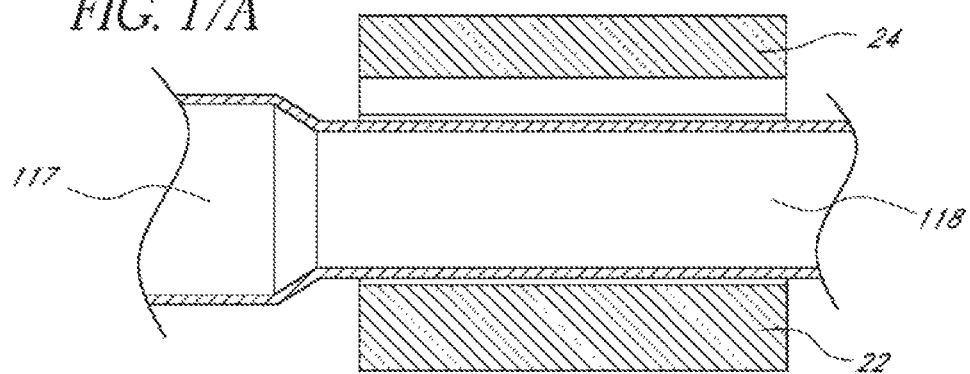
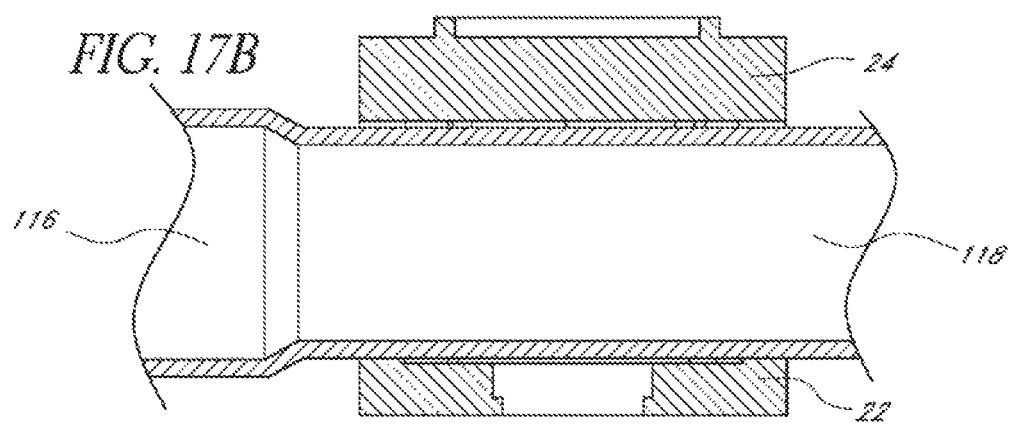
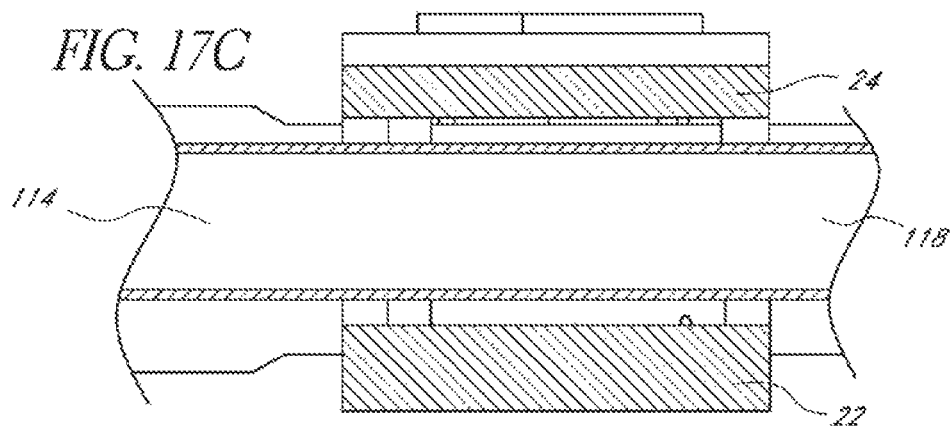

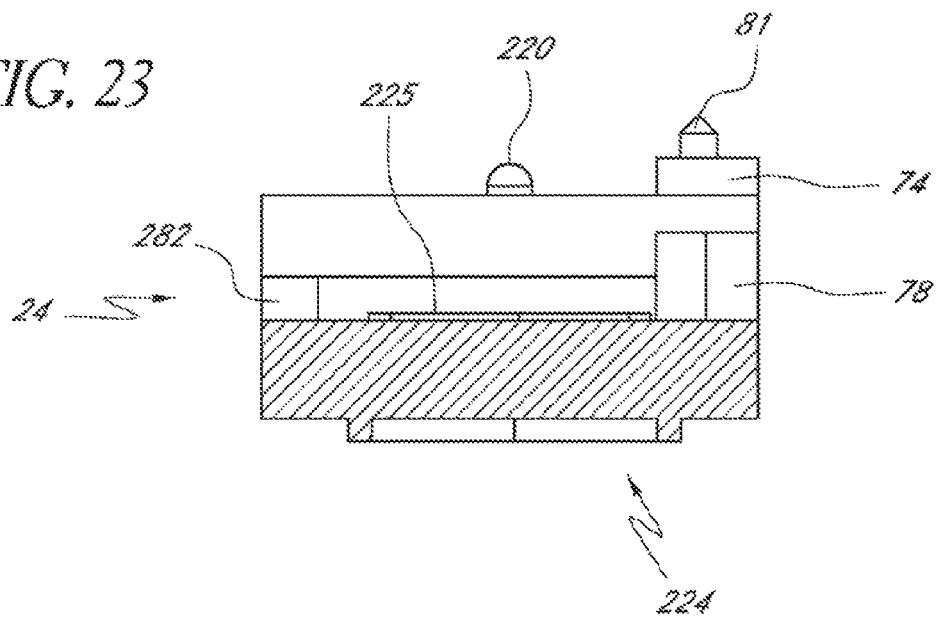
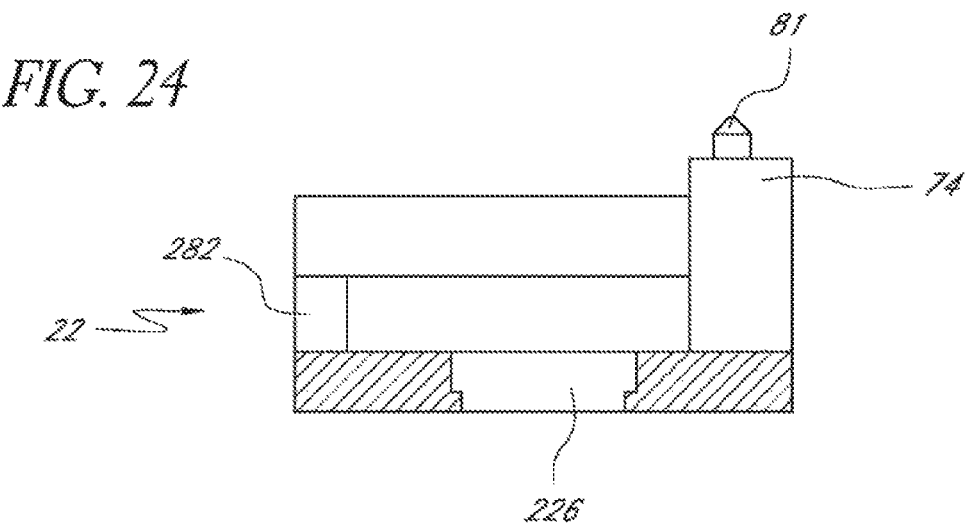

*FIG. 25*
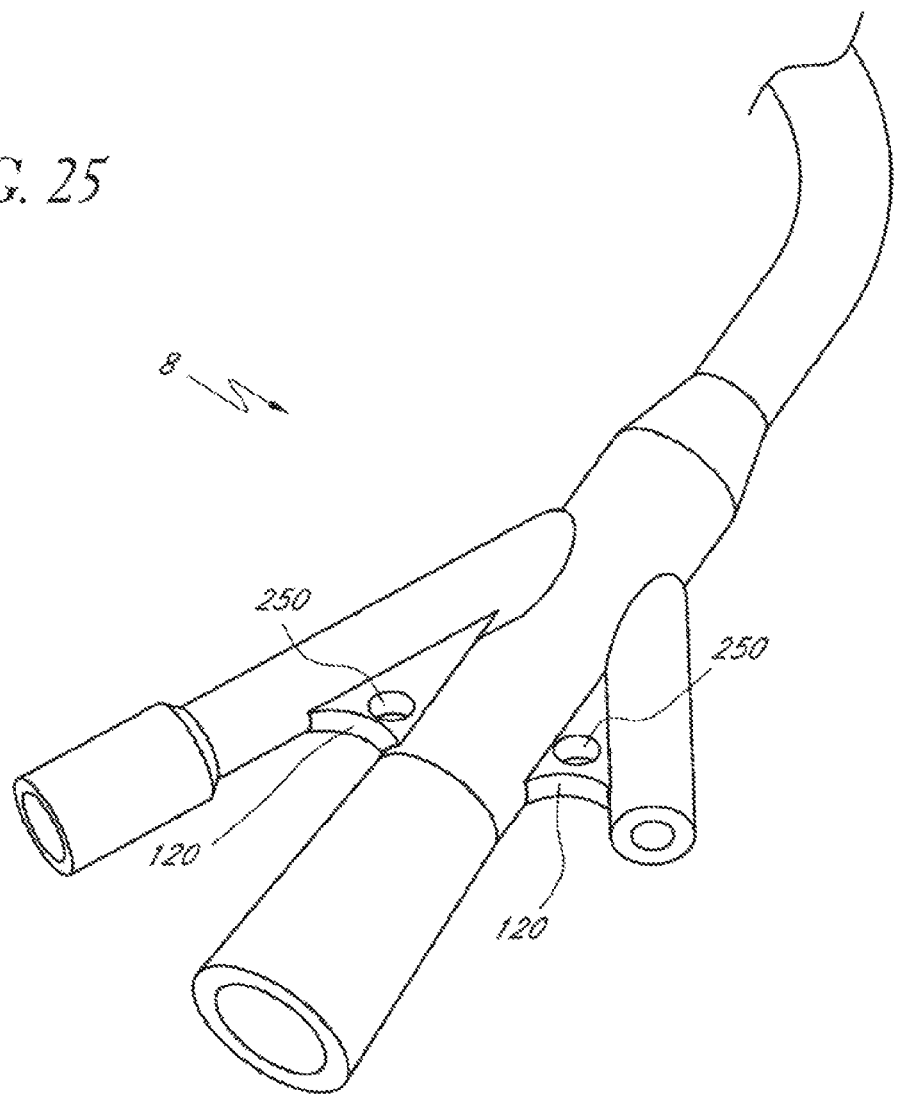
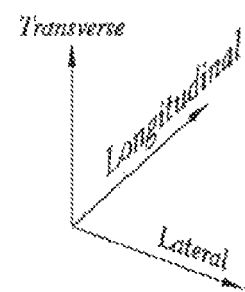

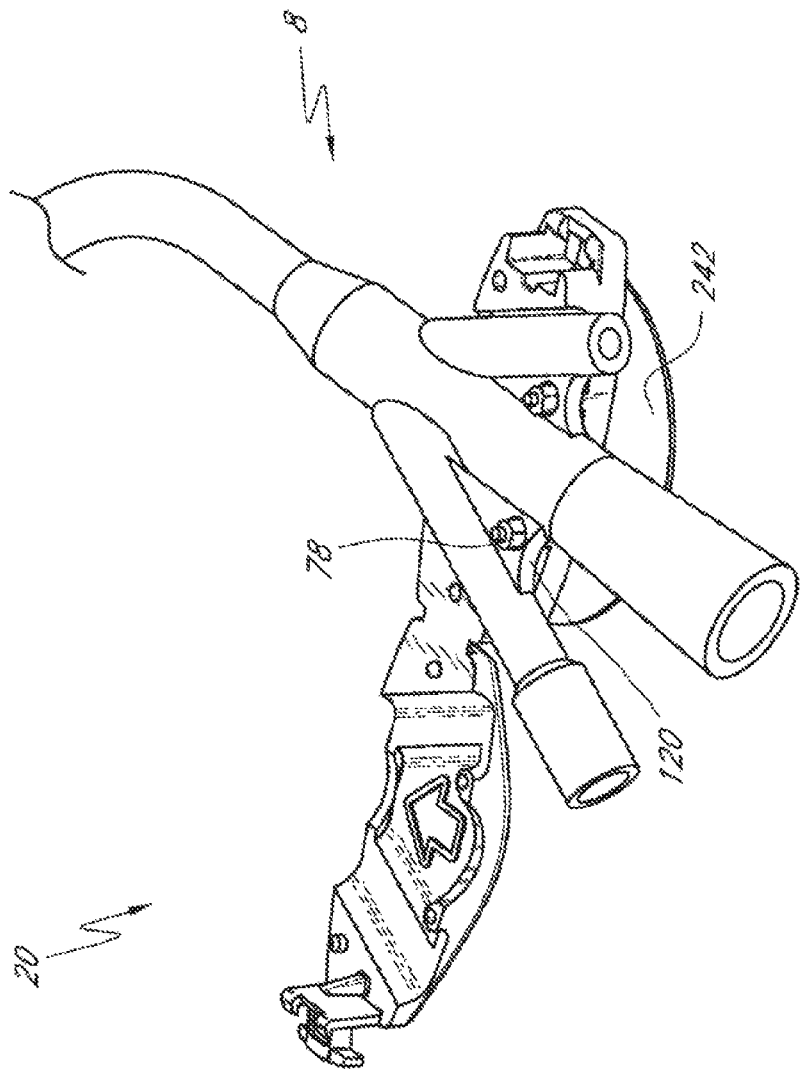
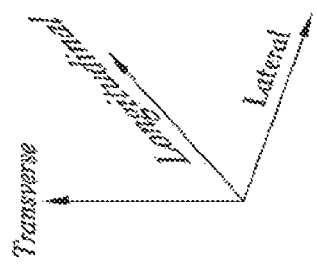
FIG. 27

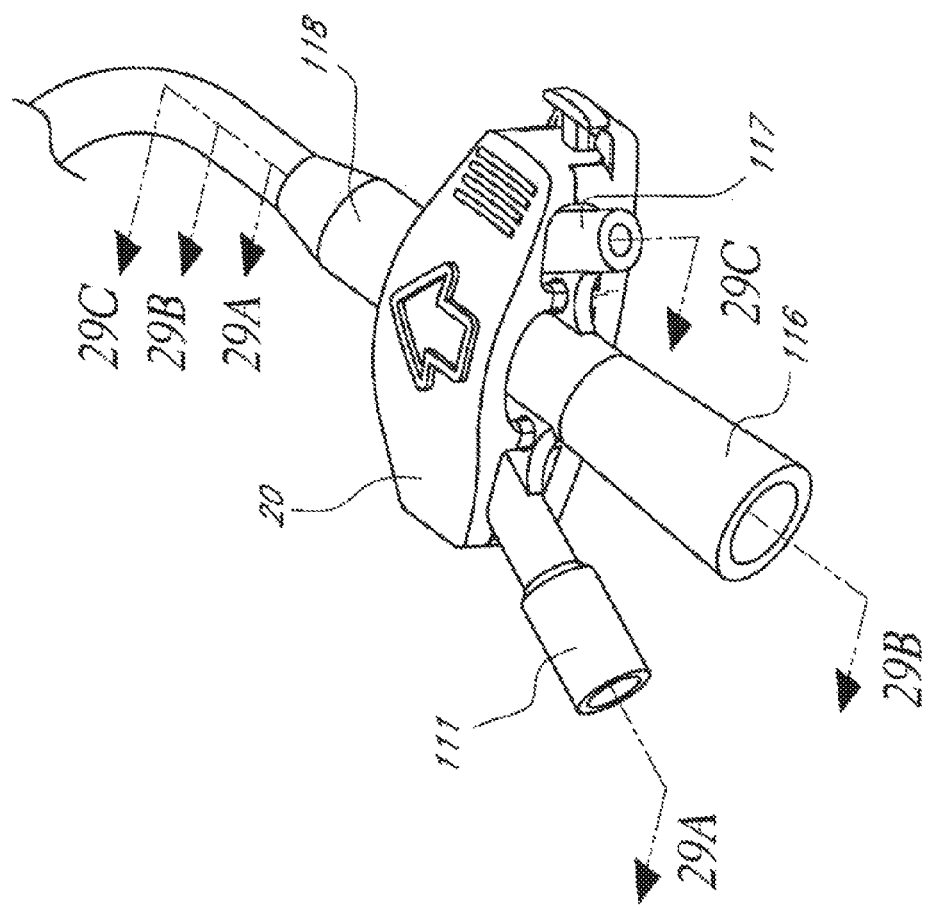
FIG. 28
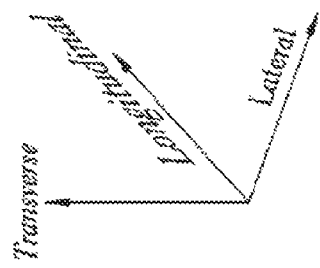

ANCHORING SYSTEM FOR A MEDICAL ARTICLE

PRIORITY

This application is a continuation of U.S. patent application Ser. No. 13/001,924, now U.S. Pat. No. 9,480,821, which is a national stage application of International Application No. PCT/US2008/068854, filed Jun. 30, 2008, titled "Anchoring System for a Medical Article," each of which is incorporated by reference in its entirety into this application.

BACKGROUND OF THE INVENTION

Field of the Invention

The present invention relates to an anchoring system for securing a medical article to a patient to inhibit movement or migration of the medical article relative to the patient.

Description of the Related Art

Hospitalized patients often have limited mobility due either to their condition or to doctor's orders. Such patients must lie in bed and not move about their hospital room, even to urinate. As such, a Foley catheter is often used with the bed-confined patient to drain urine from the patient's bladder. Use of a Foley catheter thus eliminates toilet trips as well as reduces bedpan use.

A Foley catheter may include three coaxial lumens: a drainage lumen, an inflation lumen, and an auxiliary lumen. The inflation lumen communicates with an inflation balloon located at the tip of the catheter (i.e., the catheter proximal end). The proximal end of the drainage lumen includes one or more influent openings to receive urine from the bladder. The lumens usually diverge in a trident pattern at the distal end of the catheter to form an effluent port, an auxiliary port, and an inflation port.

In use, a healthcare provider inserts the Foley catheter through the urinary tract of the patient to locate the tip of the catheter within the patient's bladder. The healthcare provider often applies lubricant to the outer surface of the catheter. The provider then inflates the balloon by attaching the inflation port to a source of pressurized working fluid (e.g., saline solution). Once inflated, a valve, which is located at the inflation port, inhibits the flow of fluid from the inflation lumen and the balloon to keep the balloon inflated. The inflated balloon prevents the catheter from unintentionally dislodging from the bladder. The healthcare provider then connects the distal end of the drainage lumen (i.e., its effluent port) to a drainage tube leading to a collection container. The third lumen may be intermittently connected to a source of liquids to irrigate the bladder.

The healthcare provider usually secures the distal end of the Foley catheter to the patient using tape. The healthcare provider commonly places long pieces of tape across the distal end of the catheter in a crisscross pattern to secure the catheter distal end to the inner thigh of the patient. This securement inhibits disconnection between the catheter and the drainage tube, as well as prevents the catheter or drainage tube from snagging on the bed rail or other objects.

Taped connections, however, often collect contaminants and dirt. Normal protocol therefore requires periodic tape changes in order to inhibit bacteria and germ growth at the securement site. Frequent tape changes though lead to another problem: excoriation of the patient's skin. In addition, valuable time is spent applying and reapplying the tape to secure the catheter. And healthcare providers often remove their gloves when taping because most find the taping procedure difficult and cumbersome when wearing gloves. Not only does this further lengthen the procedure, but it also subjects the healthcare provider to possible infection.

SUMMARY OF THE INVENTION

Embodiments of the present invention involve several features for an anchoring system useful for the securement of a medical article to a patient's body. Without limiting the scope of this invention, its more prominent features will be discussed briefly. After considering this discussion, and particularly after reading the Detailed Description of the Preferred Embodiments section below in combination with this section one will understand how the features and aspects of these embodiments provide several advantages over prior securement devices.

One aspect of the present invention is a catheterization system that secures at least a portion of a catheter. The system can include a catheter, retainer, latching mechanism, and an anchor pad. The catheter can have an elongated body and a branching site with at least three elongated sections extending from the branching site. The retainer can include a base, a cover and at least two posts. The cover can be moveable with respect to the base between an open position and a closed position. The base and the cover further can have generally curvilinear grooves that together form a channel when the cover is in the closed position. The posts on the retainer can be disposed in the channel so that the channel and the posts define a shape that generally matches the shape of the branching site and the elongated sections of the catheter. Further, each post can have a contact surface configured to abut against the catheter at the branching site, inhibiting movement of the secured portion of the catheter in at least one direction. The channel and the at least two posts can also support the secured portion of the catheter at least when the cover is in the closed position. The latching mechanism can be operable between the base and the cover to releasably secure the cover to the base. The anchor pad can support the retainer. The anchor pad can also have an upper surface and a lower surface, at least a portion of the lower surface being formed with an adhesive layer for contacting a patient's skin.

Another aspect of the invention is a catheterization system that secures a silicone catheter. The system can include a catheter, an anchor pad, a retainer, at least one protrusion, and a latching mechanism. The catheter can have an elongated body and a branching site, at least three elongated sections extending from the branching site. The anchor pad can have an upper surface and a lower surface, at least a portion of the lower surface being formed with an adhesive layer to which the retainer can attach. The retainer can also include a base and a cover. The base can comprise a first generally curvilinear groove and the cover can be movable with respect to the base between an open position in which the first groove is exposed and a closed position in which at least a portion of the first groove is covered. The cover can include a second generally curvilinear groove that cooperates with the first groove when the cover is in the closed position to define a channel having a shape that substantially matches a shape of the catheter. The channel can further be configured to support the secured portion of the silicone catheter. The at least one protrusion can be disposed in the channel and have a rounded distal end, with at least the distal end interacting with the catheter when the cover is in the closed position. The latching mechanism can operate between the base and the cover to releasably secure the cover to the base.

Another aspect of the invention is a securement device for securing an elongated medical article. The device includes an anchor that has an upper surface and a lower surface. At least a portion of the lower surface is formed with an adhesive layer. The device further includes a retainer that has a base and a cover. The cover is moveable with respect to the base between an open position and a closed position. Each of the base and the cover has a generally curvilinear groove. The grooves together form a channel when the cover is in the closed position. The channel supports the secured portion of the catheter at least when the cover is in the closed position. The device further includes a latching mechanism operable between the base and the cover to releasably secure the cover to the base when the cover is in the closed position. The latching mechanism includes a keeper, a latch, a latch post, and a latch post receiving portion. The keeper has at least one member capable of interengaging with at least a portion of the base, and the latch has a recess for accepting at least a portion of the member when the cover is in the closed position. The latch post interengages with the latch post receiving portion so as to structurally support the latching mechanism when the cover is in the closed position.

Another aspect of the invention is a retainer for securing a catheter having an elongated body, a branching site, and at least three elongated sections extending from the branching site. The retainer can comprise a base and a cover, the cover being moveable with respect to the base between an open position and a closed position. Each of the base and the cover can have a generally curvilinear groove, with each groove extending between longitudinal ends of the retainer and forming a channel when the cover is in the closed position. The channel formed by the grooves can have one or more recesses, formed in the base and in the cover, configured to receive a portion of the catheter. Each recess can have a longitudinal length less than a longitudinal length of the retainer so as to form a ridge at each end of the channel. Each ridge in the cover can then cooperate with the corresponding ridge in the base when the cover is in the closed position to define a portion of the channel. The retainer can further comprise a latching mechanism operable between the base and the cover to releasably secure the second side of the cover to the second side of the base.

Another aspect of the invention is a method of releasably anchoring a silicone catheter including a branching site onto a patient. An anchoring device having an adhesive lower surface and a retainer supported by the anchoring device can be provided. The retainer can have a base, a cover, and at least two retaining members. The base can have generally curvilinear proximal and distal rims, at least one protrusion, and a recessed portion disposed between said rims. Further, the base and the cover can together form a channel when the cover is secured in a position over at least a portion of the base. At least a branching site of the silicone catheter can be inserted into the recessed portion of the base such that at least one branch of the silicone catheter lies to each side of each of the at least two retaining members of the base. The cover can be positioned over at least a portion of the base. The cover can be secured in a position overlying the covered portion of the base, the secured cover pressing at least a portion of the silicone catheter against the at least one protrusion to inhibit movement of the secured portion of the catheter relative to the retainer. Further, the anchoring device can be secured to the skin of the patient via the adhesive lower surface of the anchoring device.

Another aspect of the invention is a catheterization system for securing at least a portion of a catheter. The system can comprise a catheter, a retainer, a latching mechanism, and an anchor pad. The catheter can have an elongated body, a branching site, at least two elongated sections extending from the branching site, and a webbing between the elongated sections comprising at least one hole. The retainer can include a base, a cover, and at least one post. The cover can be moveable with respect to the base between an open position and a closed position. Each of the base and the cover can have a generally curvilinear groove, the grooves together forming a channel when the cover is in the closed position. The at least one post can be disposed in the channel so that the channel and the at least one post define a shape that generally matches a shape of the branching site and the at least two elongated sections of the catheter. At least when the cover is in the closed position the at least one post is configured to pass through the at least one hole in the webbing of the catheter. The channel and the at least one post support the secured portion of the catheter. The latching mechanism can operate between the base and the cover to releasably secure the cover to the base. The anchor pad can support the retainer, with an upper surface and a lower surface. At least a portion of the lower surface can be formed with an adhesive layer for contacting a patient's skin.

These and other aspects of the present invention will become readily apparent to those skilled in the art from the following detailed description of the preferred embodiments, which refers to the attached figures. The invention is not limited, however, to the particular embodiments that are disclosed.

BRIEF DESCRIPTION OF DRAWINGS

These and other features, aspects, and advantages of the anchoring system disclosed herein are described below with reference to the drawings of preferred embodiments, which are intended to illustrate and not to limit the invention. Additionally, from figure to figure, the same reference numerals have been used to designate the same components of an illustrated embodiment. Like components between the illustrated embodiments are similarly noted as the same reference numbers with a letter suffix to indicate another embodiment. The following is a brief description of each of the drawings.

FIG. 5 illustrates a plan view of the retainer from the anchoring system of FIG. 1 showing the exterior surfaces of the retainer with the cover in the open position;

FIG. 6 illustrates a plan view of the retainer from the anchoring system of FIG. 1 showing the interior surfaces of the retainer with the cover in the open position;

FIG. 7 illustrates a side view of the retainer taken along lines 7-7 in FIG. 6;

FIG. 8 illustrates a side view of the retainer taken along lines 8-8 in FIG. 6;

FIG. 9 illustrates a cross-sectional view of the cover of the retainer from FIG. 6 along the lines 9-9;

FIG. 10 illustrates a cross-sectional view of the base of the retainer from FIG. 6 along the lines 10-10;

FIG. 10A illustrates a cross-sectional side view of the base from FIG. 10 assembled to a mounting base for rotation;

FIG. 10B illustrates an enlarged cross-sectional view from FIG. 10A showing a post of the mounting base engaged with a hole in the base of the retainer;

FIG. 13 illustrates a perspective view of a catheter to be retained by the anchoring system illustrated in FIG. 1;

FIG. 14 illustrates the catheter from FIG. 13 aligned with the anchoring system of FIG. 1;

FIG. 15 illustrates the catheter of FIG. 13 inserted in the retainer of FIG. 4;

FIGS. 17A-C illustrate cross-sectional views of the catheter and retainer of FIG. 16 along the lines 17A-17A, 17B-17B, and 17C-17C, respectively;

FIG. 23 illustrates a cross-sectional view of the retainer from FIG. 22 along the lines 23-23;

FIG. 24 illustrates a cross-sectional view of the retainer from FIG. 22 along the lines 24-24;

FIG. 25 illustrates a perspective view of a catheter to be retained by the retainer from FIG. 21;

FIG. 27 illustrates the catheter of FIG. 25 inserted in the retainer of FIG. 21;

FIG. 28 illustrates the retainer of FIG. 26 in a closed position; and

DETAILED DESCRIPTION

Figure 1:
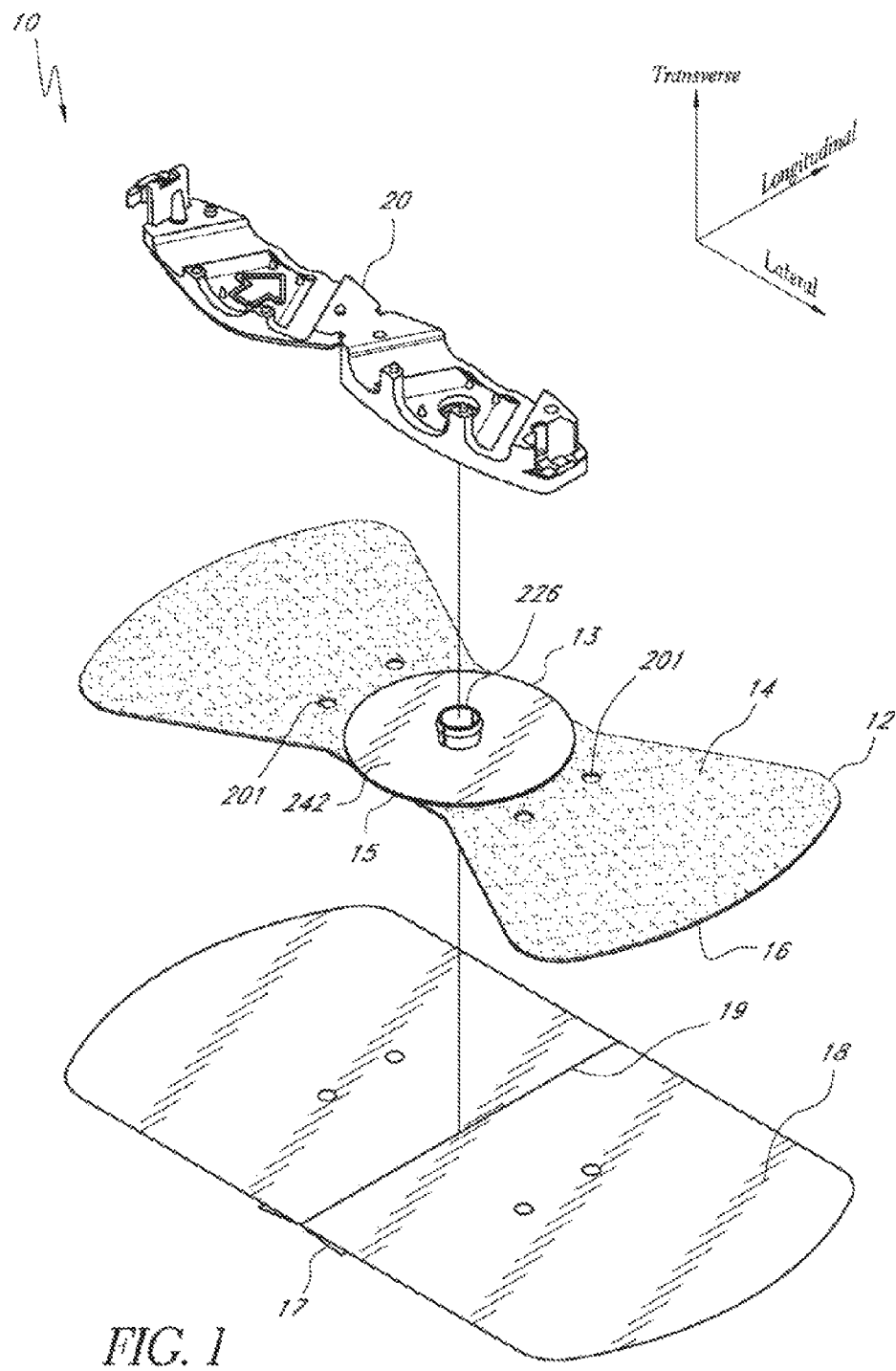
FIG. 1 is an exploded, perspective view of a preferred embodiment of an anchoring system configured in accordance with the present invention and shows a cover of a retainer in an open position.

The present embodiment of the medical article anchoring system is disclosed in the context of an exemplary 3-way Foley type catheter. The principles of the present invention, however, are not limited to 3-way Foley catheters. Instead, it will be understood by one of skill in this art, in light of the present disclosure, that the anchoring system and retainer disclosed herein also can be successfully utilized in connection with other types of medical articles, including other types of catheters, fluid drainage and delivery tubes and electrical wires. For example, but without limitation, the retainer disclosed herein can also be configured to receive and secure central venous catheters, peripherally inserted central catheters, hemodialysis catheters, surgical drainage tubes, feeding tubes, chest tubes, nasogastric tubes, scopes, as well as electrical wires or cables connected to external or implanted electronic devices or sensors. One skilled in the art can also find additional applications for the devices and systems disclosed herein. Thus, the illustration and description of the anchoring system in connection with a Foley catheter is merely exemplary of one possible application of the anchoring system.

The anchoring system described herein is especially adapted to arrest axial movement of a catheter with a slippery coating, as well as hold a catheter against the patient. For this purpose, the anchoring system 10 utilizes one or more retention elements. The anchoring system accomplishes this though without meaningfully impairing (i.e., substantially occluding) the fluid flow through the catheter to a degree that would create complications. As described below, such retention elements involve, among others, the shape of the channel that retains a section of the catheter, a retaining member either aligned with or positioned within the channel, a securement protrusion(s) and/or friction ridge(s) that bites into the catheter body without substantially occluding the catheter drainage lumen, and/or cooperating members that come together to clamp onto or pin a portion of the catheter (e.g., a webbing formed between the branches at the Foley catheter branching site).

The anchoring system also desirably releasably engages the catheter. This allows the catheter to be disconnected from the anchoring system, and from the patient, for any of a variety of known purposes. For instance, the healthcare provider can want to remove the catheter from the anchoring system to ease disconnection of the catheter from the drainage tube or to clean the patient. The disengagement of the catheter from the anchoring system, however, can be accomplished without removing the anchoring system from the patient.

Before describing the present anchoring system in detail, a brief description of a Foley catheter is provided to assist the reader's understanding of the exemplary embodiment that follows. As best understood from FIG. 13, the catheter 8 includes a proximal tip with an inflatable balloon (not shown) and a distal end 110. The distal end 110 includes a branching site 112 formed by an inflation branch 114, auxiliary branch 117, and a drainage branch 116. The branches 114, 116, 117 merge together at the branching site 112. The lumens of these branches assume either a coaxial or side-by-side arrangement on the proximal side of the branching site 112 to form a main catheter body 118. On the distal side of the branching site 112, a webbing 120 can extend between the branches 114, 116, 117 next to the branching site 112. As shown in the illustrated embodiment, the drainage branch 116 can be positioned in between the auxiliary branch 117 and the inflation branch 114. As further depicted, the drainage branch 116 can comprise a generally circular shape with a diameter greater than the other branches 114, 117. It will be clear from the disclosure herein that the branches can be configured in other orders and comprise other shapes (e.g. generally elliptical, square, triangular, etc.) and sizes. As illustrated in FIGS. 17A-C and 29A-C, these branches can be retained by a cover 24 and base 22 of the retainer 20.

In various embodiments, the auxiliary branch 117 can be configured to perform one or more different functions. In some embodiments the auxiliary branch 117 comprises an irrigation branch (as shown). The irrigation branch can allow fluid to be passed from a distal portion to a proximal portion. This fluid can then wash an internal cavity of a patient and flow back out through the drainage branch 116. As another example, in some embodiments the auxiliary branch 117 is configured as a thermocouple branch. The thermocouple branch can include a thermocouple. The thermocouple can extend through the main catheter body 118 and measure the temperature at a proximal end of the catheter 8. At the distal end of the thermocouple branch an electronic connection can be provided to allow a user to connect the thermocouple to an electronic device. The electronic device can translate an input voltage, current, or other electrical property sensed by the thermocouple into a human-perceivable temperature measurement or indication. Measurements of other characteristics of the patient, catheter, and/or fluids passing within the auxiliary branch 117 are also within the scope of the invention as would be understood by those skilled in the art.

Figure 2:
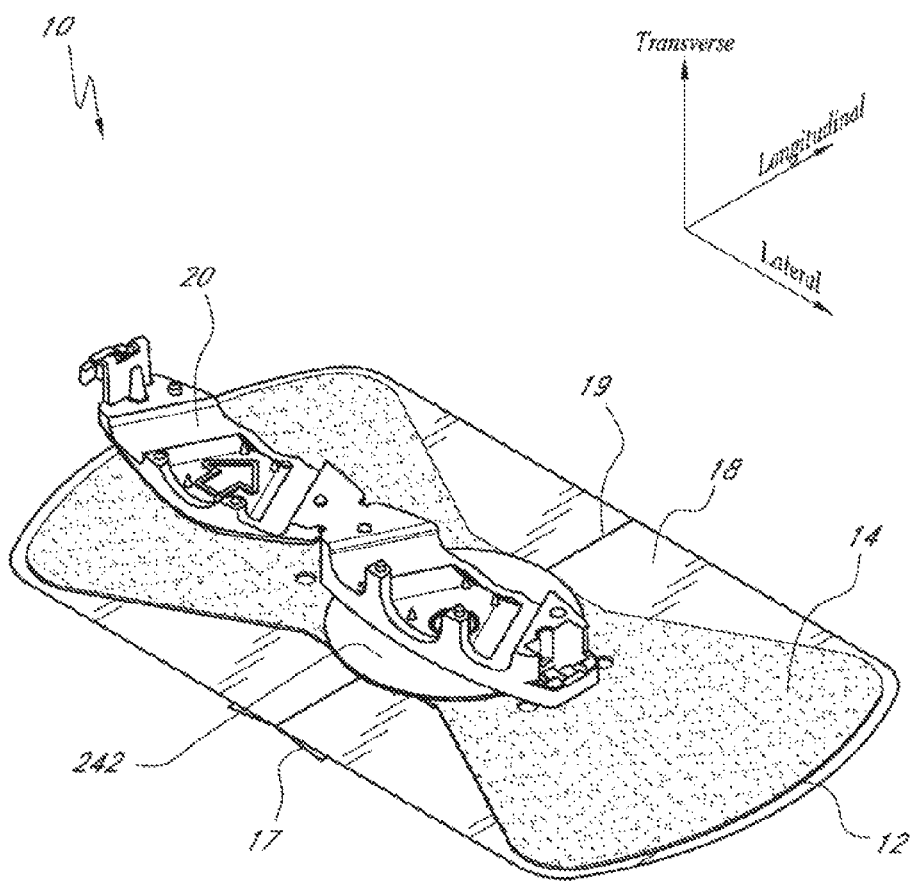
FIG. 2 illustrates a perspective view of the anchoring system of FIG. 1 with the retainer assembled to an anchor pad.
Figure 3:
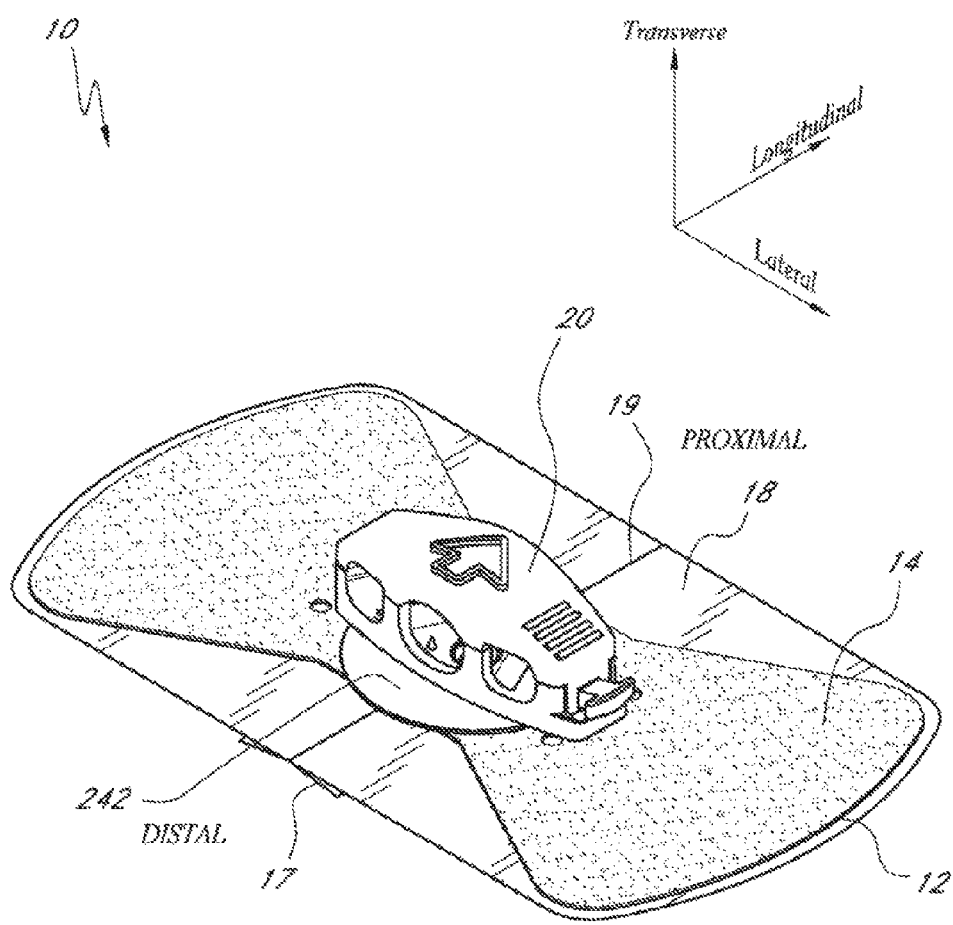
FIG. 3 illustrates a perspective view of the anchoring system of FIG. 1 with the cover in a closed position.

With reference now to FIGS. 1-3, the anchoring system 10 includes an anchor pad 12 and a retainer 20. The anchor pad 12 secures the retainer 20 to a patient's skin. The anchor pad 12 has a lower adhesive surface 16 which adheres to the skin of a patient and a roughened upper surface 14 which supports a retainer 20.

The anchoring system 10 may further include a mounting base 242. The mounting base 242 connects the retainer 20 to the anchor pad 12 and allows the retainer 20 to rotate relative to the anchor pad 12. The retainer 20 preferably rotates by at least some degree, and more preferably by 360 degrees, relative to the anchor pad 12. For this purpose, in the illustrated embodiment, a mounting post 226 is attached to the anchor pad 12 and a hole 232 is formed in the base 22 of the retainer 20. However, the anchoring system 10 need not include the mounting base 242. In other embodiments, the retainer 20 directly connects to the anchor pad 12 and does not rotate relative to the anchor pad 12.

The retainer 20 is configured to accept and retain a section of a Foley catheter 8 within the anchoring system 10. In the illustrated embodiment, the retainer 20 comprises a base 22 and a cover 24. The cover 24 is detachably secured to the base 22 and moveable between open and closed positions.

To assist in the description of these components of the anchoring system 10, the following coordinate terms are used. A "longitudinal axis" is generally parallel to the section of the catheter 8 retained by the anchoring system 10. A "lateral axis" is normal to the longitudinal axis and is generally parallel to the plane of the anchor pad 12. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. Also, the terms "proximal" and "distal", which are used to describe the present anchoring system 10, are used consistently with the description of the exemplary application. Thus, proximal and distal are used in reference to the center of the patient's body. A detailed description of the anchoring system 10, and its associated method of use, now follows.

FIGS. 1-3 illustrate an anchor pad 12 which desirably comprises a laminate structure with an upper foam layer (e.g., closed-cell polyethylene foam), and a lower adhesive layer. The lower adhesive layer constitutes the lower surface 16 of the anchor pad 12. The lower surface 16 desirably is a medical-grade adhesive and can be either diaphoretic or non-diaphoretic, depending upon the particular application. Such foam with an adhesive layer is available commercially from Avery Dennison of Painsville, Ohio. Further, the anchor pad 12 can include suture holes 201 in addition to the adhesive layer 16 to further secure the anchor pad 12 to the patient's skin.

A surface of the upper foam layer constitutes an upper surface 14 of the anchor pad 12. The upper surface 14 can be roughened by corona-treating the foam with a low electric charge. The roughened or porous upper surface 14 can improve the quality of the adhesive joint (which is described below) between the retainer 20 and the anchor pad 12. In the alternative, the flexible anchor pad 12 can comprise a medical-grade adhesive lower layer, an inner foam layer and an upper paper or other woven or nonwoven cloth layer.

A removable paper or plastic release liner 18 desirably covers the adhesive lower surface 16 before use. The liner 18 preferably resists tearing and desirably is divided into a plurality of pieces to ease attachment of the pad to a patient's skin. In the illustrated embodiment, the liner 18 is split along a center line 19 of the flexible anchor pad 12 in order to expose only half of the adhesive lower surface 16 at one time.

The liner 18 length, as measured in the lateral direction, extends beyond the center line 19 of the anchor pad 12 and is folded over, or back onto the liner 18. This folded over portion defines a pull tab 17 to facilitate removal of the liner 18 from the adhesive lower surface 16. A healthcare provider uses the pull tab 17 by grasping and pulling on it so that the liner 18 is separated from the lower surface 16. The pull tab 17 overcomes any requirement that the healthcare provider pick at a corner edge or other segment of the liner 18 in order to separate the liner 18 from the adhesive layer. The pull tab 17 of course can be designed in a variety of configurations. For example, the pull tab 17 need not be located along a center line 19 of the anchor pad 12; rather, the pull tab 17 can be located along any line of the anchor pad 12 in order to ease the application of the anchor pad 12 onto the patient's skin at a specific site. For example, an area of a patient's skin with an abrupt bend, such as at a joint, can require that the pull tab 17 be aligned toward one of the lateral ends of the anchor pad 12 rather than along the center line 19.

In the illustrated embodiment, the anchor pad 12 also desirably includes a pair of opposing concave sections 13, 15 that narrows the center of the anchor pad 12 proximate to the base 22. As a result, the lateral sides of the anchor pad 12 have more contact area which provides greater stability and adhesion to a patient's skin.

With reference now to FIGS. 4-10, the retainer 20 includes a rigid structure principally formed by the base 22 and the cover 24. In the illustrated embodiment, the base 22 and cover 24 are integrally formed to comprise a unitary retainer 20. This can be accomplished in any of a variety of ways well known to those skilled in the art. For instance, the entire retainer 20 can be injection molded to reduce fabrication costs.

Additionally, as will be apparent from the below description, several features of the retainer 20 (e.g., a latch keeper and a hinge) desirably are flexible. In some embodiments, it will be desirable to use materials that are capable of producing shapes that are flexible in defined areas but rigid in other areas. Suitable ridged but flexible materials include, for example, but without limitation, plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermo set plastics and the like. The illustrated retainer 20 preferably is formed by injection molds using polyethylene or polypropylene material. However, other materials can be utilized, and the retainer 20 can comprise a non-unitary base 22 and cover 24.

Figure 4:
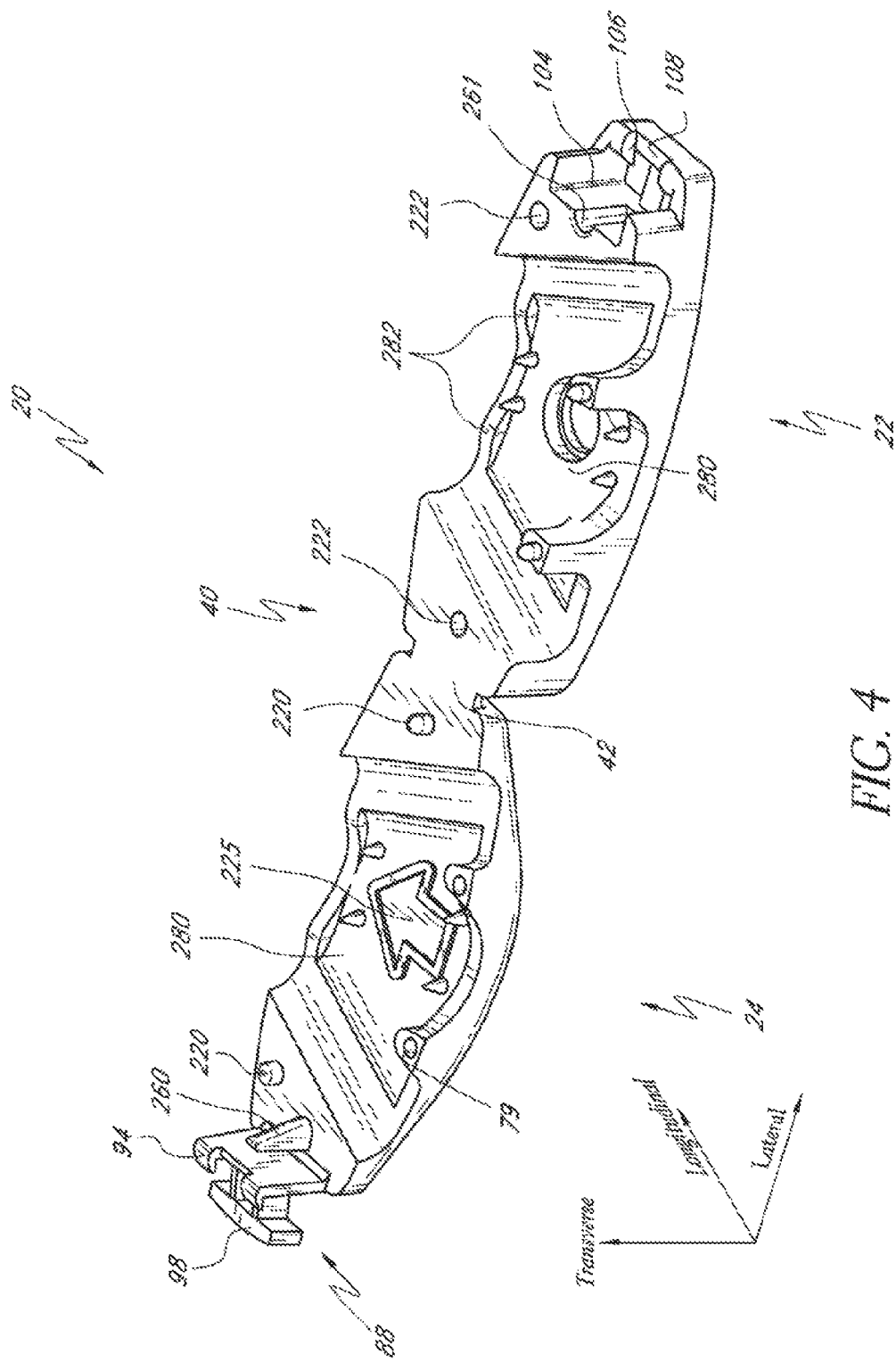
FIG. 4 illustrates a perspective view of the retainer from the anchoring system of FIG. 1 with the cover in an open position.

With reference to FIG. 4, a base 22 in the illustrated embodiment comprises an elongated body of a generally parallelepiped shape. The base 22, however, can be configured in a wide variety of shapes as well, such as circular, square, triangular or the like in order to suit a particular application. The longitudinal dimension of the base 22 desirably is sufficiently long to provide stability to the catheter 8 along its length. That is, the longitudinal length of the retained catheter portion is sufficient to inhibit rocking of the catheter 8 relative to the retainer 20 (i.e., to prevent the retainer 20 from acting as a fulcrum for the catheter). Also, the lateral dimension of the base 22 desirably allows the healthcare provider to easily and naturally grip the base 22, as well as provides space on which to locate a hinge 40 and a portion of the latch mechanism 80. As will be clear from the description herein, other embodiments of the retainer 20 may be desirably short, so as to allow the retainer 20 to act as a fulcrum in any one or more dimensions. For example, in some embodiments it may be desirable to allow more play in the angle of the catheter 8 near the retainer 20 (e.g. if the retainer 20 is generally close to the patient-insertion point, but not angularly aligned therewith).

As best depicted in FIGS. 5 and 6, the base 22 includes first and second sides 26, 28. The first side 26 lies generally at one lateral end of the base 22, and the second side 28 lies at an opposite lateral end of the base 22.

A groove 30 is formed on the base 22 between the first side 26 and the second side 28. In the illustrated embodiment, the groove 30 has a generally curvilinear cross-sectional shape. As best seen in FIGS. 6, 10, the lower groove 30 is also varied in width (i.e., in the lateral direction) along its longitudinal length. That is, in the illustrated embodiment, the side walls of the lower groove 30 diverge from each other in a generally linear manner from one longitudinal side of the retainer 20 to the other longitudinal side of the retainer.

The base 22 of the retainer 20 is supported by the upper surface 14 of the anchor pad 12. In the illustrated embodiment, the mounting base 242 desirably is secured to the upper surface 14 by a solvent bond adhesive, such as cyanoacrylate or other bonding material. One such adhesive is available commercially as Part No. 4693 from the Minnesota Mining and Manufacturing Company (3M).

As also seen in FIGS. 5, 6, the cover 24 can have an elongate shape which desirably is coextensive with the planar size and shape of the base 22 (i.e., desirably has the same general geometric shape and size as the base 22); however, the cover 24 need not be the same size or shape as the base 22. For instance, the cover 24 can be sized to extend beyond any of the lateral, traverse, or longitudinal edge of the base 22 or, alternatively, can be sized so as to not extend to the lateral, traverse, or longitudinal edge of the base 22. The cover can also include a skirt or flange that extends over and/or about the base 22 or any portion thereof.

The cover 24 though desirably has a sufficient size to cover the lower groove 30 in the base and to accommodate a portion of the latch mechanism 80 and the hinge 40 which operate between the base 22 and the cover 24, as described below. The cover 24 also desirably is of a dimension which provides for easy manipulation. For example, the cover's size easily accommodates the grasp of a healthcare provider.

The cover 24 includes a first side 32 which lies generally at one lateral end of the cover. The first side 32 of the cover 24 therefore generally corresponds to the first side 26 of the base 22. The cover 24 also comprises a second side 34. The second side 34 lies generally toward a lateral end of the cover 24, opposite of the first end, and corresponds generally to the second side 28 of the base 22.

An upper groove 36 is formed on an inner side of the cover 24 between the first and second sides 32, 34 of the cover 24 and corresponds generally to the lower groove 30 formed in the base 22. The width of the upper groove 36 is also varied in the lateral direction along its longitudinal length. That is, in the illustrated embodiment, the side walls of the upper groove 36 diverge from each other in a generally linear manner from one longitudinal end of the cover 24 to the other longitudinal end.

The cover 24 is flexibly coupled to the base 22 by way of a flexible coupling or hinge 40. The coupling 40 desirably comprises a flexible band 42 that can take any number of forms to mechanically connect the cover 24 to the base 22 while permitting pivotal movement of the cover 24 relative to the base 22 so as to enable engagement or disengagement of these parts, as described below. In the illustrated embodiment, the band 42 is formed of flexible material, desirably of the same material from which the base 22 and cover 24 are comprised. Advantageously, the hinge 40 is integrally molded with the base 22 and the cover 24 to form a unitary member, as noted above. The hinge 40 is located at an outer edge of the base 22 and the cover 24; however, the hinge 40 need not be laterally located at an extreme end of the base 22 or cover 24.

As best understood from FIG. 5, the width of the hinge 40, as measured in the longitudinal direction, is desirably less than that of either the base 22 or the cover 24 to allow some leeway or play when engaging or disengaging the cover 24 to the base 22. That is, this shape allows the hinge 40 to twist to some degree to compensate for some manufacturing tolerances; however, the hinge 40 can have at least as large of a longitudinal dimension as the base 22 and the cover 24.

The hinge 40 is desirably integrally formed along a common corresponding exterior surface of the cover 24 and base 22. In the illustrated embodiment, as best understood from FIGS. 7, 8, the hinge 40 has generally a U-shape, and extends from both the base 22 and the cover 24 in the lateral direction to the side of the retainer 20. A gap (not shown), corresponding to a transverse height of the hinge 40, exists between the base 22 and cover 24, near the hinge when in the closed position. This gap, however, can be reduced or eliminated from the retainer 20 for some applications by using a different hinge design.

The hinge 40 enables the cover 24 to move between the open position and the closed positions. The open position, as illustrated in FIG. 4, is characterized by exposing at least a portion of the grooves 30, 36 in the base 22 and the cover 24 in the transverse direction and thereby spacing apart the base 22 and the cover 24. When in the open position, the retainer 20 is capable of receiving a portion of a Foley catheter 8 (e.g., the branching site 112). The closed position, as illustrated in FIG. 3, is characterized by the cover 24 lying in contact or near contact with the base 22 so as to position the upper groove 36 above the lower groove 30. When in the closed position, the retainer 20 substantially surrounds the received portion of the catheter.

The hinge 40 need not provide 180 degrees of movement of the cover 24 relative to the base 22 to establish the closed position and a fully open position, as illustrated by FIGS. 3, 4. For instance, the hinge 40 can permit a smaller degree of movement (e.g., 90 degrees) between the base 22 and the cover 24 while still providing enough space to transversely insert the catheter into the retainer 20.

Figure 18:
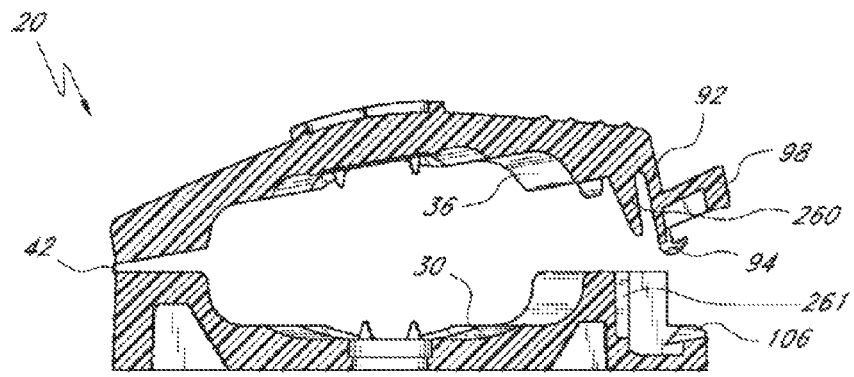
FIG. 18 illustrates the retainer of FIG. 4 in an intermediate position.
Figure 19:
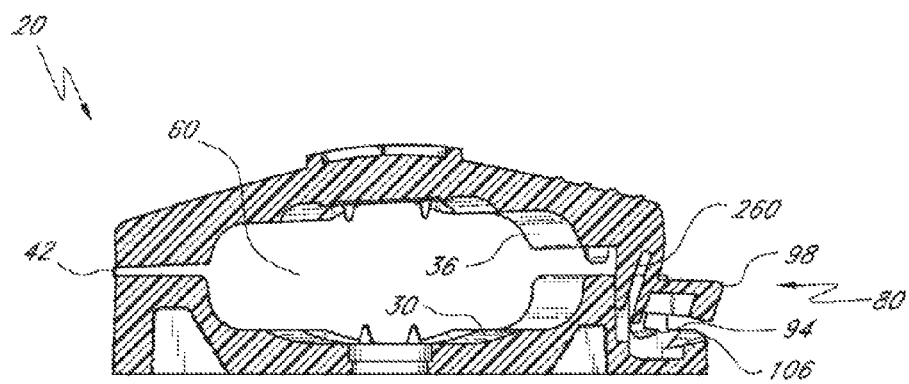
FIG. 19 illustrates the retainer of FIG. 4 near a closed position.
Figure 20:
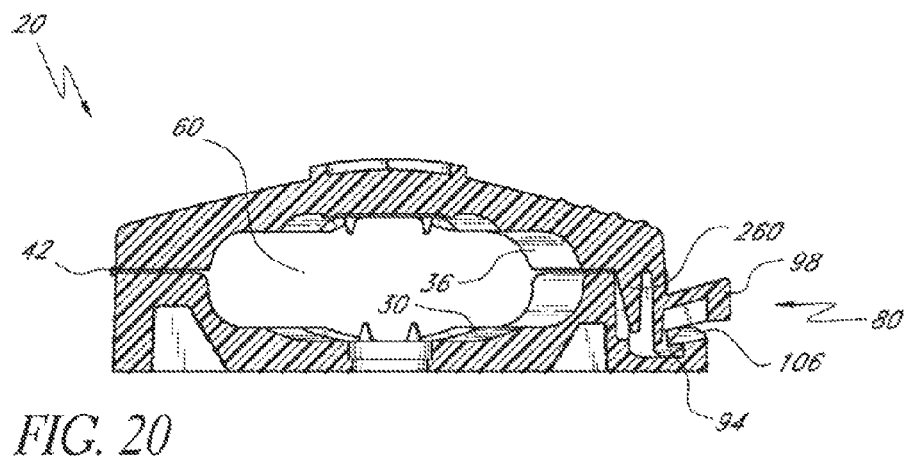
FIG. 20 illustrates the retainer of FIG. 4 in a closed position.
Figure 21:
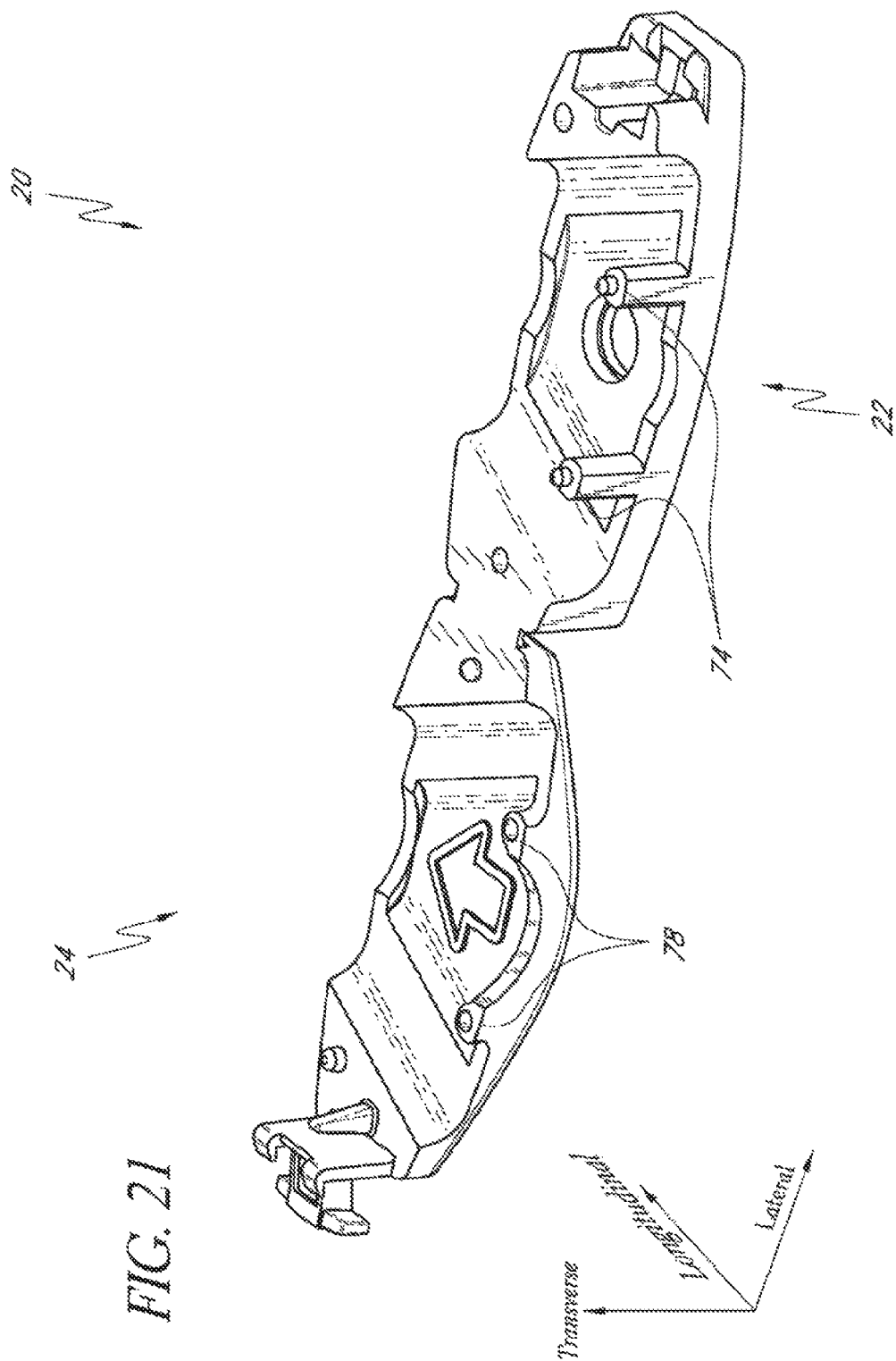
FIG. 21 illustrates a perspective view of another embodiment of the retainer with the cover in an open position.
Figure 22:
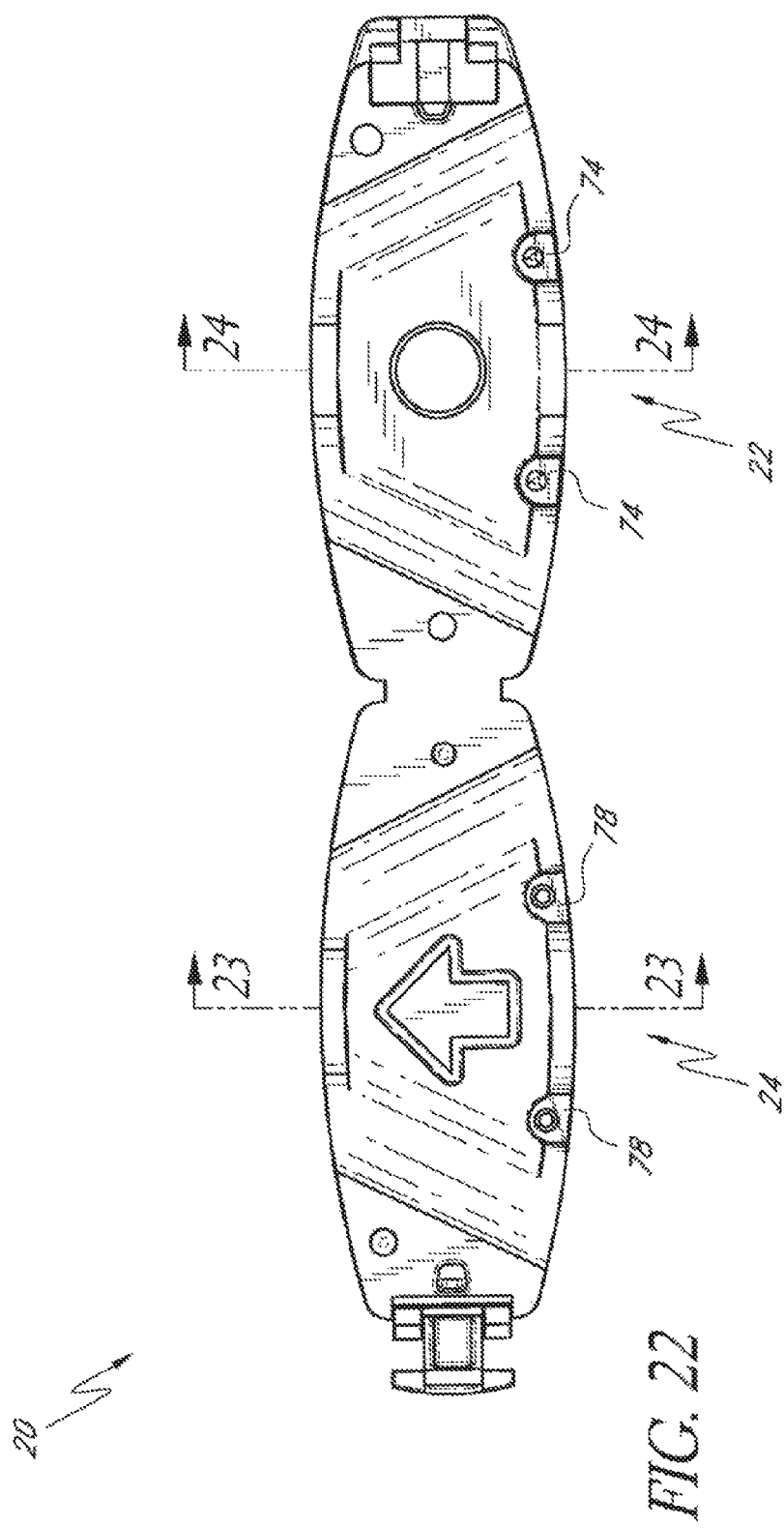
FIG. 22 illustrates a plan view of the retainer from FIG. 21 showing the interior surfaces of the retainer with the cover in the open position.
Figure 26:
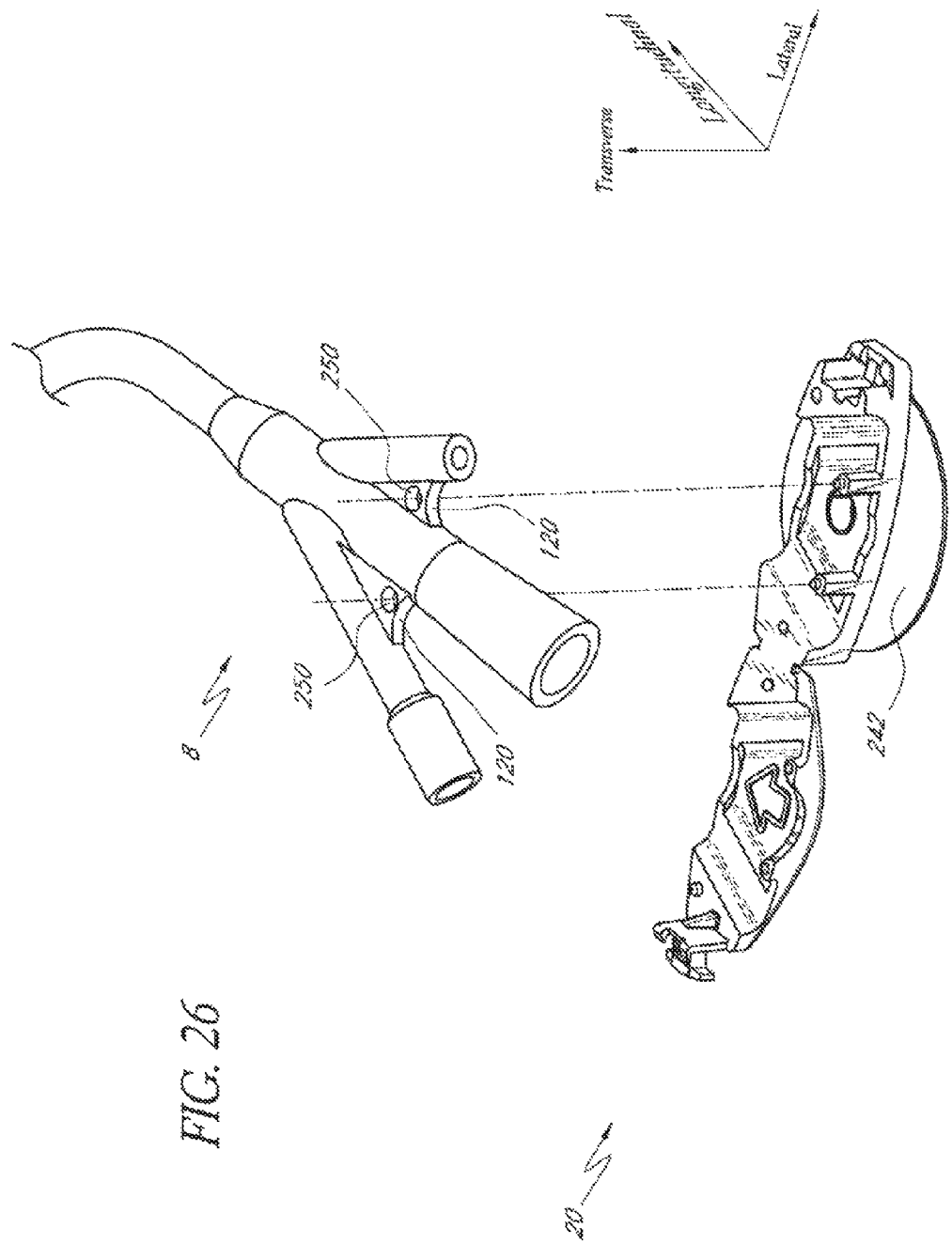
FIG. 26 illustrates the catheter from FIG. 25 aligned with the retainer of FIG. 21.
Figure 29A:
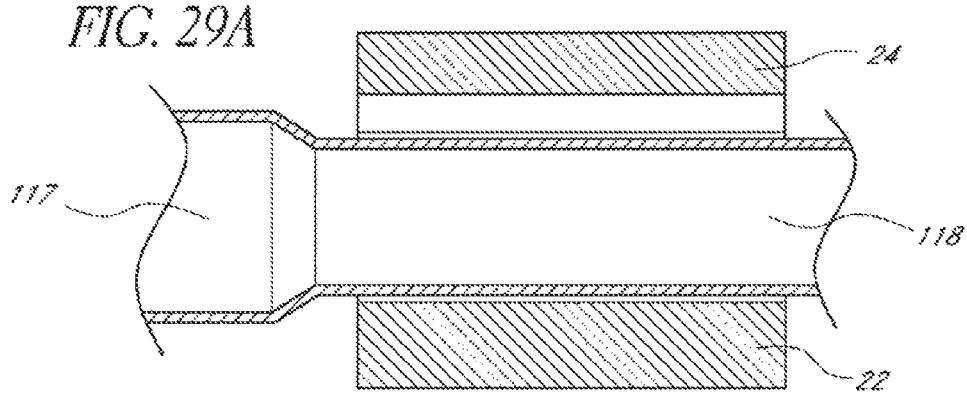
FIGS. 29A-C illustrate cross-sectional views of the catheter and retainer of FIG. 28 along the lines 29A-29A, 29B-29B, and 29C-29C, respectively.
Figure 29B:
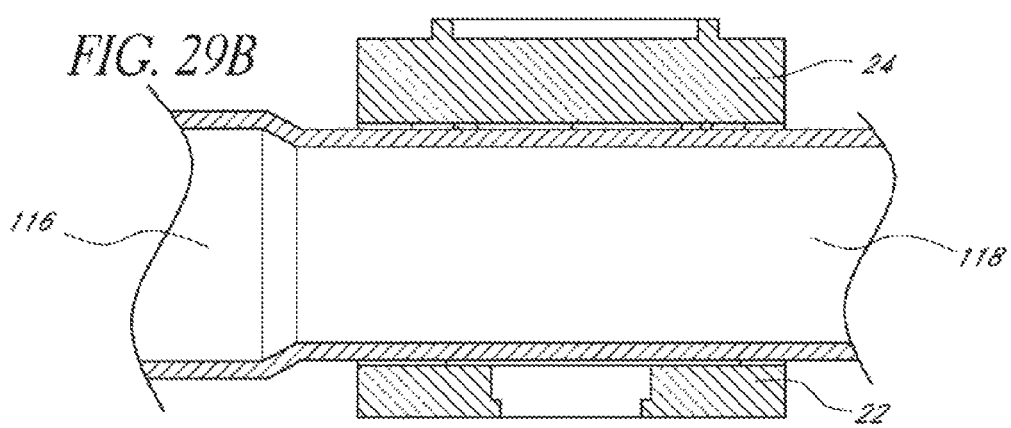
Figure 29C:
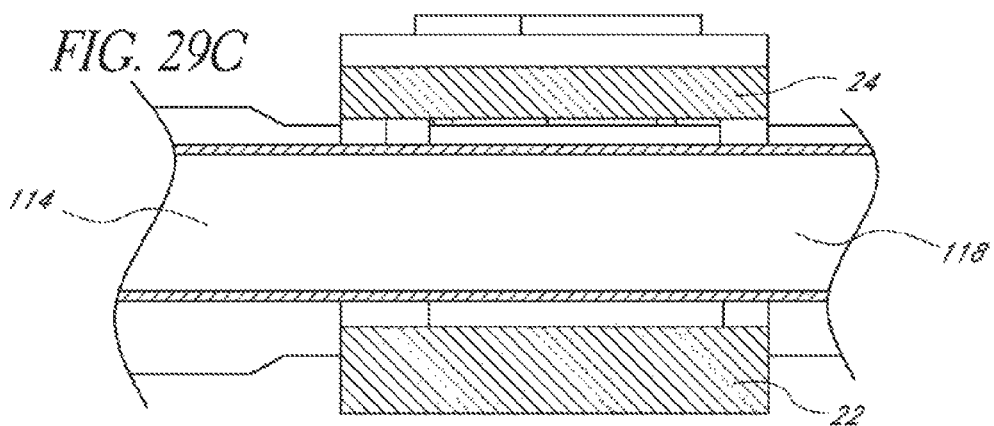

As best illustrated in FIGS. 18-20, the grooves 30, 36 formed in the base 22 and the cover 24 define a channel 60 when the retainer 20 is closed. The channel 60 is capable of receiving a portion or length of the catheter 8 and is generally configured to house, grip and secure the affected catheter portion. The channel 60 can have a variety of configurations, as discussed above in connection with the grooves 30, 36, in order to accommodate a particular medical article. In the illustrated embodiment, the channel 60 generally has rounded cross-sectional shapes at its proximal end and a generally oblong cross-sectional shape at its distal end (although, in the illustrated embodiment, the distal end is divided by pairs of cooperating posts, which will be described below). The channel 60 smoothly tapers in cross-sectional size from its smaller proximal end to its larger distal end. The channel 60 consequently generally has a truncated V-shape, as best understood by inspecting the shapes of the grooves 30, 36 in FIG. 6. In a preferred embodiment, the channel 60 can be shaped and sized to substantially match the catheter 8.

In the embodiment illustrated in FIGS. 1-10, the lateral sides of the channel 60 are generally straight and diverge from each other. The walls of the channel 60 (and, thus, the grooves of the cover and base), however, need not be straight. For example, the wall of the base groove 30 can have a convex bulge (not shown) that narrows the portion of the channel that receives the inflation branch 114 of the catheter. This channel shape furthers retention of the catheter within the channel 60 to inhibit catheter movement through the channel, as discussed below.

Although the channel 60 can take the form of various shapes depending upon its application (i.e., depending upon a shape of the retained portion of the medical article 8 for which the retainer is designed to be used), the channel 60 preferably has a sufficient length in the longitudinal direction to stabilize the catheter, rather than act as a fulcrum for the catheter, as mentioned above. That is, the retainer preferably receives a sufficient length of the catheter 8 to inhibit movement of the catheter in the lateral, longitudinal and transverse direction (i.e., to inhibit yaw, pitch and axial movement of the catheter), without kinking the catheter. Also, the wide-mouth shape (i.e., the large oval-shape) of the channel proximal opening eliminates an edge or surface over which the catheter could kink. It will be clear from the disclosure herein, that a shorter retainer 20 may be used if other movement inhibiting elements are included, or if certain movements of the medical article 8 are tolerable.

When the cover 24 is closed, a section of the catheter 8 is captured within the retainer 20. Thus, the retainer 20 at least restricts, if not prevents, lateral and transverse movement of the retained section of the catheter 8.

Inhibiting movement of the catheter 8 in the longitudinal direction when the catheter 8 is secured within the channel 60 is desirably accomplished by one or more retention elements that associate with the channel 60. With reference to FIG. 6, one such retention element involves the shape of the channel 60 itself. The interaction between the truncated V-shape of the channel 60 and a corresponding shape of the catheter branching site 112 inhibits proximal longitudinal movement.

Figure 15A:
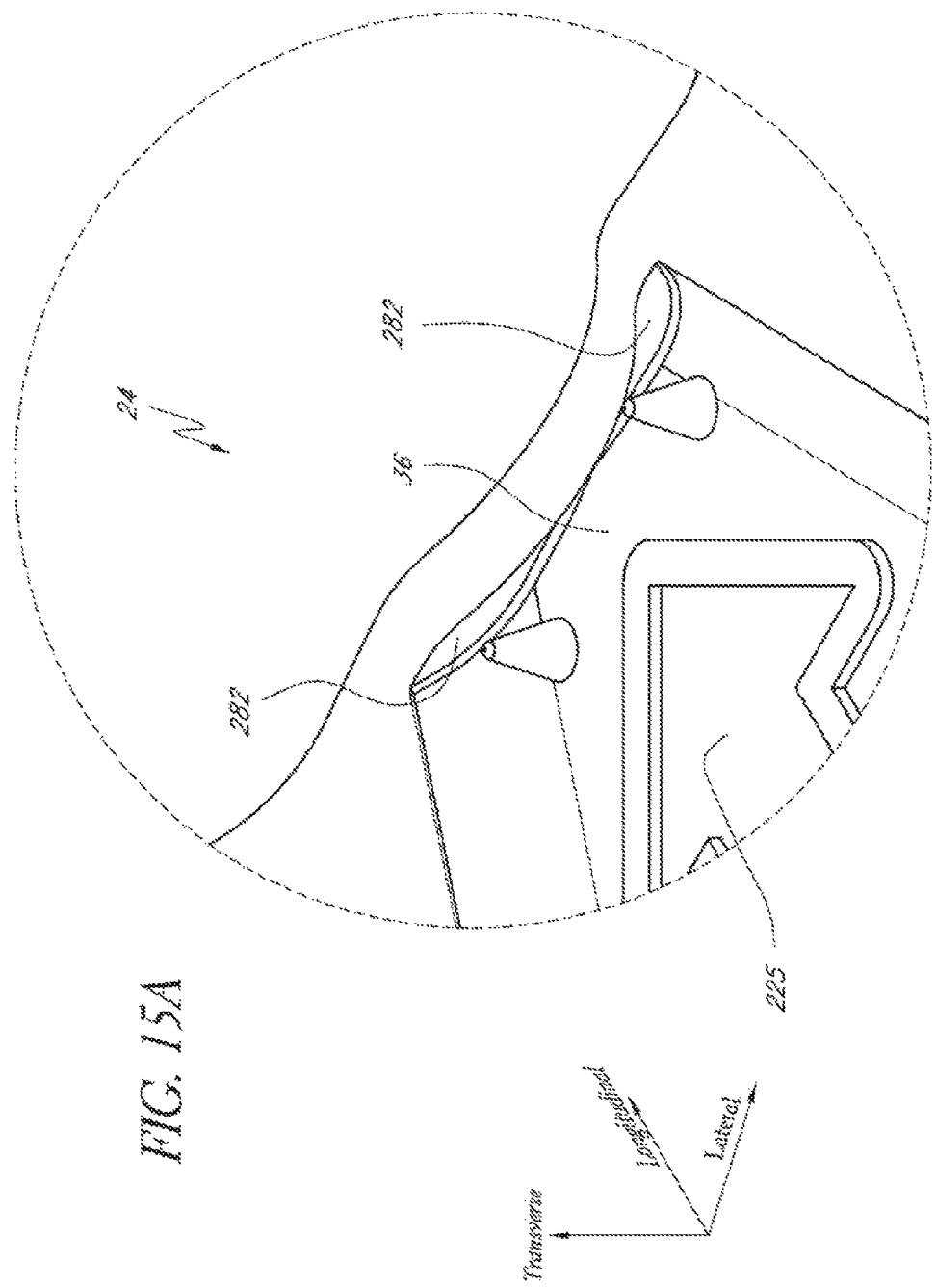
FIG. 15A illustrates an enlarged perspective view of the retainer of FIG. 4 in an open position.

As best understood from FIGS. 14, 15 the proximal end of the channel 60 is sized to receive only the main body 118 of the catheters. The distal end of the channel 60 is sized to receive the branches 114, 116, 117 (i.e., the inflation lumen section, the auxiliary lumen section, and the drainage lumen section) at the distal side of the branching site 112. And between its distal and proximal ends, the channel 60 is configured to receive the catheter branching site 112.

Figure 12:
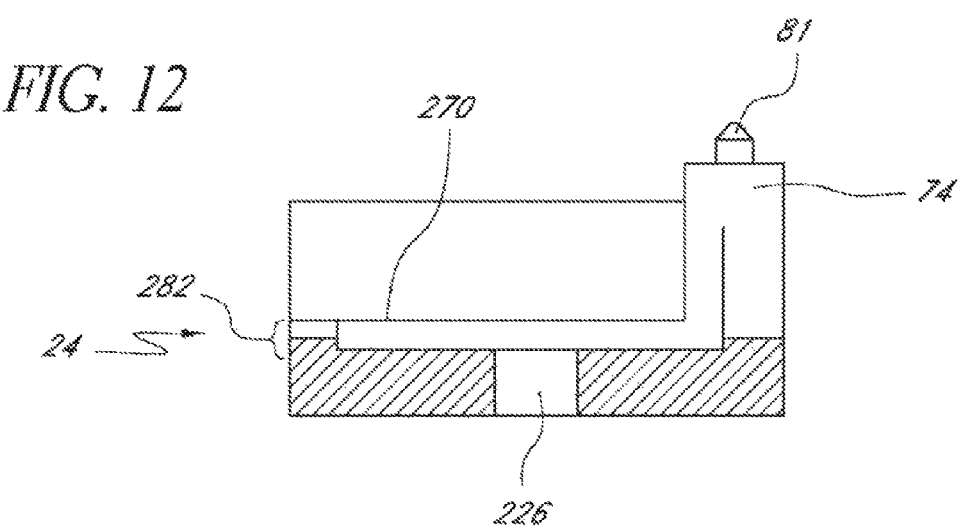
FIG. 12 illustrates a cross-sectional view of the retainer from FIG. 6 along the lines 12-12.

Because the catheter branching site 112 is larger in cross-section than its main body 118 and because of the presence of a large valve which is attached to the catheter inflation branch (see FIG. 12), the branching site 112 usually cannot be pulled proximally through the smaller proximal end of the retainer channel 60. The shape of the channel 60 thus inhibits longitudinal movement of the catheter in the proximal direction.

Figure 11:
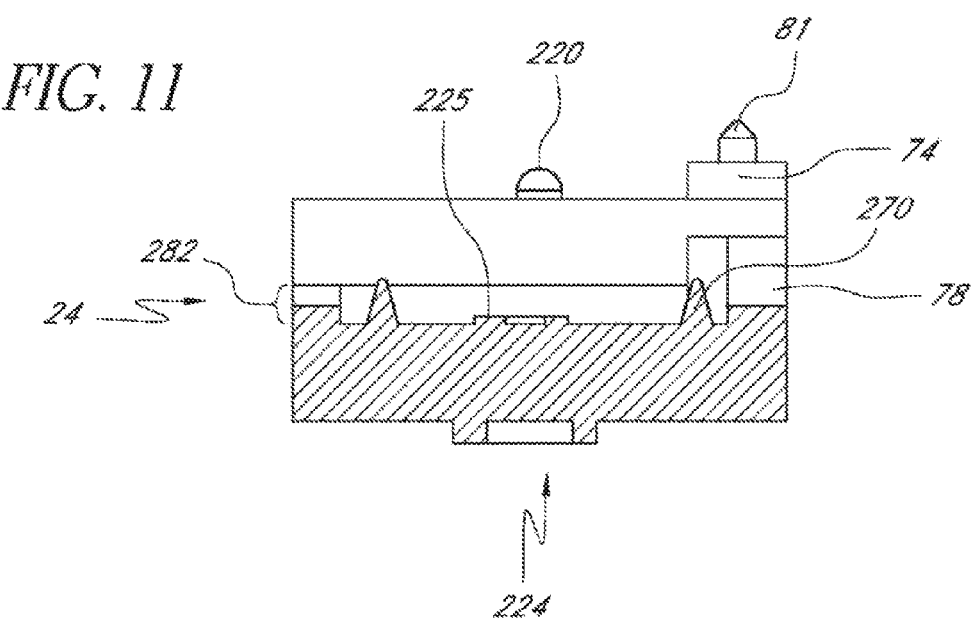
FIG. 11 illustrates a cross-sectional view of the retainer from FIG. 6 along the lines 11-11.

As best shown in FIGS. 9, 10, the channel 60 can further comprise recessed portions 280 on both the cover 24 and base 22. The recessed portions 280 illustrated are substantially flat with curved edges 281 along their lateral sides. On both longitudinal sides of the recessed portions 280, the retainer 20 can comprise rims 282 (best illustrated in FIGS. 11, 12, and 15A) that are substantially curved and generally match the corresponding portions of the catheter 8. The rims 282 can be oriented generally in the transverse-lateral plane, generally perpendicular to the channel 60. Further, the rims 282 can generally slope to match the channel 60 in the center of the channel 60 and/or near the curved edges 281. As will be described below, the recessed portions 280 can allow space for a catheter 8 to bulge, facilitating its securement in the retainer 20.

Variations on the channel's shape are also possible. For instance, opposing lateral sides of the channel 60 can vary from each other in a curvilinear manner and/or can include a gouge, bulge, or similar geometric abnormality so as to cooperate with or impinge upon a corresponding portion of the received catheter length. Also, there is no requirement that either or both lateral sides vary relative to an axis of the received catheter length. Either or both sides can vary in distance relative to a longitudinal axis of the received catheter length so as to inhibit longitudinal movement of the retained section of the catheter 8. The channel, however, can have a straight or uniform cross-sectional shape where the retainer includes at least another mode of the retention elements described herein.

Interaction between the surface 69 of the retainer channel 60 and the catheter branching site 112 can also create friction to inhibit longitudinal movement through the channel 60. The degree of interference between the catheter 8 and the retainer 20, however, is preferably not so great as to significantly occlude the catheter 8.

In alternative embodiments, the channel surface 69 may comprise various surface features to enhance retention of the catheter 8. For example, the channel surface 69 may comprise friction ridges (not shown). Such ridges and other surface features can be used together with or in the alternative to the other retention elements discussed herein. The ridges are desirably of smooth solid construction; however, they can be of rough and/or hollow construction. The ridges can have generally triangular cross-sectional shapes and angle toward one end of the channel 60 (e.g., the distal end), or the ridges can have other cross-sectional shapes which would interfere with axial movement of the catheter 8 through the channel 60.

One or more retaining members, which protrude into the channel 60, can also inhibit axial movement of the catheter 8. The retaining members form an upstanding member transversely positioned relative to the anchor pad 12. The retaining members are arranged to lie between the branches at the catheter branching site 112 retained by the retainer 20 so as to inhibit axial movement of the catheter 20 in the distal direction. Thus, in the illustrated embodiment, the combination of the tapering channel shape and the retaining members inhibits axial movement of the retained section of the catheter 8 in both the proximal and distal directions.

The retaining members desirably have a sufficient height to inhibit axial movement of the catheter 8 in the distal direction. For this purpose, the retaining member has a height, in the transverse direction, of at least about 25% of the height of the channel 60 at the location at which the structure is positioned. In the illustrated embodiment, the retaining member desirably extends across channel 60.

In the illustrated embodiment, each retaining member is formed by a base post 74 and a cover post 78. The base post 74 desirably is integrally formed with the base 22, and is located in the channel 60 toward the distal end of the channel 60. The cover post 78 is integrally formed with the cover 24 also at the distal end of the channel 60. Although in the illustrated embodiment, the base post 74 and cover post 78 lie within the channel 60, the posts 74, 78 can be located outside or inside the distal end of the channel 60.

In one mode, a base post 74 is sized to extend to a position where its upper end lies near or contacts the webbing 120 of the catheter 8 that extends between the branching site branches 114, 116, 117. In the illustrated embodiment, the upper end of the post 74 lies generally above a plane defined by the upper surface of the base 20 when in an open position, as best seen in FIGS. 7, 8. The cover post 78 similarly extends to a point which is generally below a plane defined by the inner surfaces of the cover (that lie adjacent to the base 22 when in a closed position), when in an open position as depicted in FIGS. 7, 8. In other embodiments, it may be desirable to provide the posts 74, 78 flush with a plane defined by the respective surfaces of the cover or the base, or reversing their positions relative to the cover or the base. In some embodiments, the base post 74 should be sufficiently large to prevent longitudinal or lateral movement of the catheter 8 when the retainer 20 is in an open position. The cover post 78 can then be sized such that, in cooperation with the base post 74, the posts form a retaining member sufficient to prevent longitudinal movement of the catheter 8 when the retainer is in a closed position.

As best seen in FIGS. 14, 15, the lateral position of the posts 74 within the channel 60 can correspond with the merge points between the branches 114, 116, 117 of the Foley catheters. The posts 74 divide the channel 60 at the channel's distal end as shown. However, as discussed, the posts 74 may divide the channel 60 at other points, including deeper within the channel, outside the channel, or at the channel's proximal end. Further, when there are multiple posts 74, as in the illustrated exemplary embodiment, each post may be provided at an approximately equal longitudinal position, or an unequal longitudinal position. For example, in some embodiments the retainer 20 may be configured to fit a catheter 8 wherein there are two branching sites (longitudinally) instead of one. In this instance, it may be desirable to position the posts 74 at accordingly different longitudinal positions to better fit the catheter 8.

The cover post 78 can be configured and arranged on the cover 24 in a manner similar to that described above in connection with the base post 74 on the base 22. In the illustrated embodiment, the post 78 thus generally opposes the base post 74. By this particular design, as understood from FIG. 6, the combination of the posts 74, 78 and the channel 60 define a generally fork-shaped recess between the channel's proximal and distal ends.

In the illustrated embodiment, the transverse height of the cover post 78 is less than that of the base post 74. The posts 74, 78, however, can have equal heights or the cover post 78 can be longer than the base post 74. Together though, the posts 74, 78 desirably span the channel 60 in the transverse direction.

The posts 74, 78 thus extend between the branches 114, 116, 117 of the catheter 8 when the catheter branching site 112 is positioned within the channel 60. Together the posts 74, 78 can act as a stop against longitudinal movement of the catheter 8 in the distal direction. That is, longitudinal movement in the distal direction causes the catheter branching site 112 to contact the posts 74, 78. The posts 74, 78, being of rigid construction, prevent further longitudinal movement.

In other embodiments, the retainer 20 may provide only one set of posts 74, 78 to retain a catheter 8 with three branches 114, 116, 117. For example, in some embodiments it may be desirable to provide a retainer 20 capable of supporting both two-branched and three-branched catheters 8, by positioning a single set of posts 74, 78 off-centered within the channel 60 such that two branches can be placed to one side of the posts. Thus, one set of posts 74, 78 can restrict the longitudinal motion of a three-branched catheter 8. Similarly, a retainer 20 with two sets of posts 74, 78 can be shaped to also accept two-branched catheters 8. In some embodiments, it may be desirable to provide a system of catheters and a retainer 20 such that a set of catheters with different numbers of branches, sizes, materials, etc. can all be retained by the same retainer 20. As an example, the set of catheters may each comprise at least one branching site with a set of branches that can be supported by the single system retainer, and if necessary also comprise further branches extending from one or more additional branching sites proximal or distal from the retainer 20.

Although the posts 74, 78 can have a variety of cross-sectional shapes, the posts 74, 78 desirably have a generally semi-circular cross-sectional shape in the present application so as to correspond to the space between the catheter branches 114, 116, 117 and/or the webbing 120 at the branching site 112. The proximal edge of the posts advantageously is rounded to eliminate sharp contact between the catheter 8 and the retainer 20 at this location. The surface of the posts 74, 78 can thus comprise a contact surface configured to abut against the branching site 112 so as to inhibit movement of the secured portion of the catheter Sin at least one direction. In other embodiments, the cross-sectional shape may be generally triangular, square, elliptical, or generally resemble some other polyhedron or smooth geometric shape, optionally matching the shape of the branches 114, 116, 117 or the webbing 120.

The posts 74, 78 can also include interengaging elements to interlock the posts 74, 78 in the transverse direction. In the illustrated embodiment, a pin or projection 81 and a corresponding receptacle 79 are arranged between the interfacing ends of the posts 74, 78. As best seen in FIGS. 4, 6, the receptacle 79 is formed at the transverse end of the cover post 78, extending into the post 78 in a transverse direction from an interface surface of the post 78. The projection 81 extends from an end of the base post 74 in a direction parallel to a transverse axis of the post 74. The projection 81 is configured to fit within the receptacle 79. When the cover 24 is closed, the projection 81 extends into the receptacle 79 to interlock together the posts 74, 78.

Figure 16:
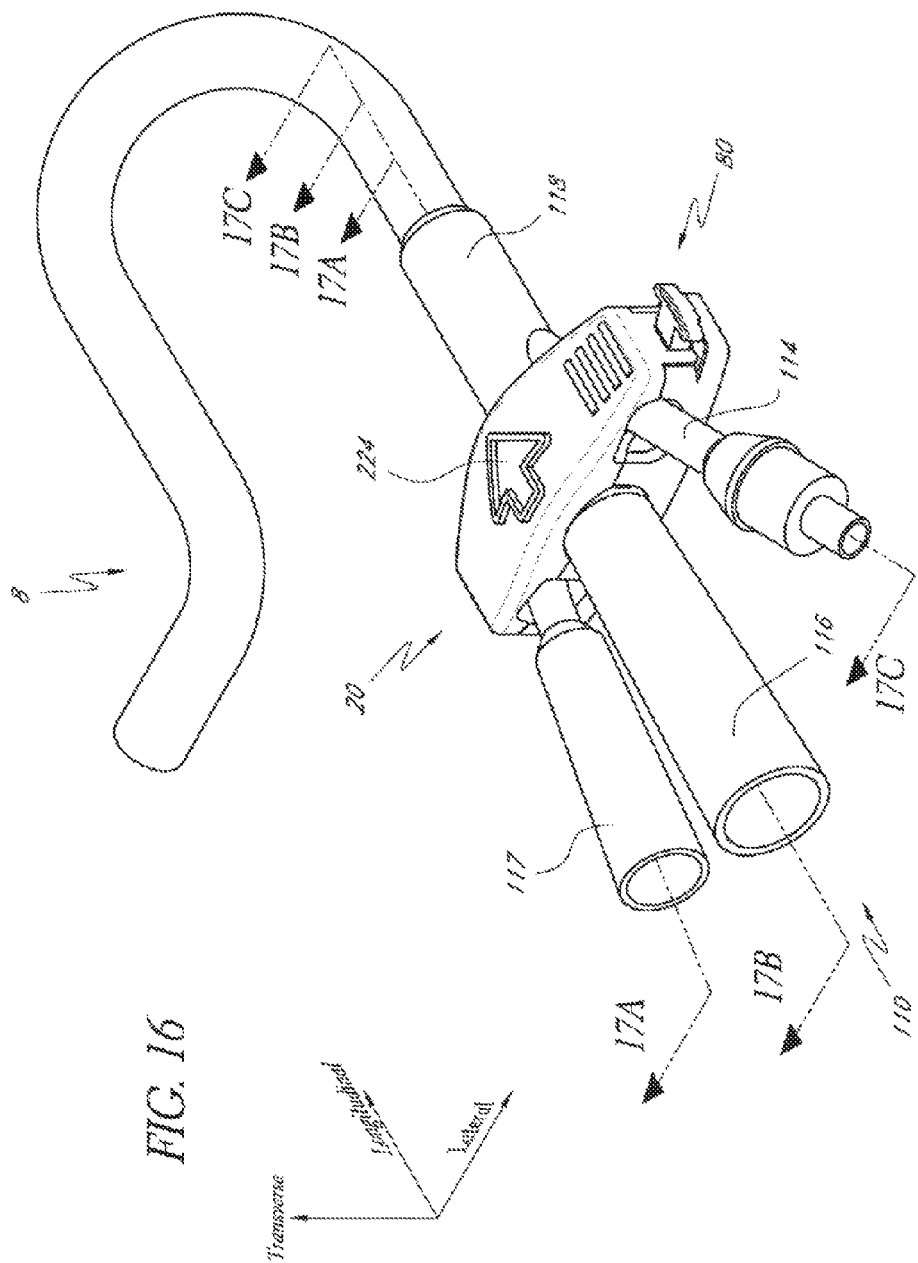
FIG. 16 illustrates the retainer of FIG. 15 in a closed position.

Another possible retention element to inhibit axial movement of the catheter 8 relative to the retainer 20 involves protuberances that are arranged to cooperate with one another when the cover 24 is closed. For instance, in one mode, the cooperating posts 74, 78 can be arranged to capture a structural portion of the catheter (e.g., the catheter webbing 120) between them without substantially occluding an inner lumen of the catheter 8, such as in FIGS. 15, 16. In another mode, the projection 81 can be employed without the receptacle 79 to simply pin a portion of the catheter (e.g., its webbing) against a surface of the retainer 20. For instance, the projection 81 can extend from a portion of either the base 22 or the cover 24 and cooperate with a corresponding surface (e.g. a post, platform or channel surface) that opposes the projection 81 when the cover is closed. The projection 81 would protrude into the portion of the catheter and pin it against the corresponding surface.

Alternatively, the projection 81 can be used with the receptacle 79 to capture a section of the catheter. When the cover 24 is closed, the projection 81 could force a portion of the catheter body 8 into the receptacle 79 to capture a structural portion of the catheter 8 between these components without occluding an inner lumen of the catheter. This engagement of the retainer 20 with the catheter body 8 would inhibit axial catheter movement relative to the retainer 20.

In another embodiment, depicted in FIGS. 21-29, the webbing 120 of the catheter 8 can be provided with receptacles or holes 250 (best shown in FIG. 25). The base posts 74 can extend through the holes 250 in the webbing 120 and interlock with the cover posts 78 to secure the catheter 8. This can secure the catheter 8 so as to prevent movement in both a proximal and distal direction. Additionally, protruding through more than one hole 250, as shown in the figures, can further prevent rotation in a plane perpendicular to the transverse direction. The base posts 74 may be shaped to fit the holes 250, and in some embodiments the holes may be oversized relative to the base posts to allow easy insertion. As a further example, in some embodiments base posts 74 can protrude through at least three non-collinear holes 250, thus preventing rotation in all dimensions (before accounting for play between the posts and holes).

One or more securement protrusions 270 can also be used to retain the catheter in the longitudinal direction. In the illustrated embodiment, each protrusion 270 has a generally conical shape with a radiused or blunt tip. The protrusion 270, in the present application, desirably extends into the channel 60 by an amount ranging between about 0.1 mm and about 3 mm.

The retainer 20 desirably includes at least one set of securement protrusions 270 arranged within the channel 60 to cooperate with one another. The protrusions 270 can advantageously be arranged collinearly on the same generally lateral line, and are spaced apart from one another. In addition, the protrusions 270 can be spaced on generally opposite surfaces 69 of the channel 60 in a staggered arrangement. That is, the position of the protrusions 270 can alternate between the cover surface and the base surface in the lateral direction. The resulting overlapping pattern of the protrusions 270 can securely hold the catheter 8 without imparting torque to the catheter 8 if pulled in a longitudinal direction. As best shown in FIG. 6, the protrusions 270 are positioned generally opposite each other, and in pairs on the surface of the cover 24 and the surface of the base 22, between the posts 74, 78. These protrusions 270 are spaced apart from one another and the pair is symmetrically positioned relative to a longitudinal axis that extends along the drainage branch 116. The distance between each pair of protrusions 270 can vary between the opposite surfaces of the channel 60. As best shown in FIG. 20, the protrusions 270 on the base surface are closer together than the protrusions on the cover surface, spreading compressive forces across the diameter of the catheter 8. In other embodiments, the protrusions 270 can be closer on the cover surface that on the base surface, or the protrusions can be staggered in some other manner such as alternatingly or longitudinally.

The drainage branch 116 can rest in between the protrusions 270 without excessive pinching of the branch 116.

The retainer 20 can also include additional sets of securement protrusions 270 arranged generally in accordance with the above description, but on another side of either of the posts 74, 78 so as to interact with the inflation or auxiliary branches 114, 117 of the catheter 8. It may be desirable to provide fewer protrusions 270, as well as fewer sets of protrusions, in these regions of the retainer 20. In some embodiments it may be desirable to angle the protrusions 270 toward either the distal end or the proximal end of the channel 60 to inhibit movement of the branches in the opposite direction. In other embodiments, for example, when other retaining members are used, the protrusions 270 might not be necessary, such as in the embodiments illustrated in FIGS. 21-29.

When securement protrusions 270 are used to hold the catheter 8, the catheter will tend to bulge around the protrusions. Thus, providing a recessed portion 280 (as discussed above) can create additional space within the channel 60 for the catheter to bulge into. By creating space for the catheter 8 to bulge outward, the catheter can accommodate the protrusions 270 without kinking inward and potentially occluding the interior lumen.

As illustrated in FIGS. 14-16, 26-28, a healthcare provider can secure a Foley catheter (or other medical article) to a patient using the above-described anchoring system (or a readily apparent modification thereof). The healthcare provider first opens the retainer 20 to expose the groove 30 on the base 22. Once opened, a catheter 8 can be transversely aligned over the groove 30. The catheter 8 can then be placed into the channel 60. If the channel 60 is formed with a post 74 (or another protuberance) for use with a branching site, the branches 114, 116, 117 are aligned around the posts 74 and the catheter branching site 112 is aligned to securely fit within the remaining groove confines. Similarly, if the base posts 74 are intended to pass through holes 250 in the catheter webbing 120, such holes and posts are also aligned. Once the catheter 8 is so aligned and placed into the groove 30, the cover 24 is closed and latched in the manner described below. The shapes of the grooves 30, 36 can ensure that the channel supports the catheter branching site 112 on at least diametrically opposed sides thereof along the entire retained length of the catheter branching site. This not only enhances frictional contact between the retainer 20 and the catheter 8, but it also prevents the catheter 8 from kinking or crimping with the retainer 20 and thereby occluding one or more of the catheter lumens.

In the illustrated embodiment, the posts 74, 78 come together with the projection 81 inserting into the receptacle 79 when the cover is closed. The posts 74, 78 therefore are interlocked in this position to form a stop on the distal side of the branching site 112 that spans entirely across the channel's transverse length. The securement protrusions 270 also can bite into the body of the catheter branching site 112 to resist movement of the catheter branches 114, 116, 117 in a direction opposite of the direction in which they are angled.

If the catheter 8 is pulled in the proximal direction, the tapered shape of the channel 60 inhibits the larger distal end of the branching site 112 and the valve on the inflation branch 114 from pulling through the retainer. An additional set of securement protrusions, which bite into the inflation and/or auxiliary lumen branches 114, 117 can also inhibit movement of the catheter in this direction. And if the retainer employs posts or projections that clamp onto, pin, or pass through the catheter webbing within the channel, then this engagement between the retainer and the catheter would further secure the catheter in place.

If the catheter discharge branch 116 is pulled in the distal direction, the interlocked posts 74, 78 inhibit this movement. The set of securement protrusions 270 bite into the discharge branch 116 and also oppose movement of the catheter branch 116 in this direction. A distal pulling force on the discharge branch 116 also tends to pull the inflation and auxiliary lumen branches 114, 117 around the posts 74, 78. Additional sets of securement protrusions can also inhibit this reaction to further anchor the catheter branching site 112 within the retainer 20.

The retainer 20 thus inhibits longitudinal movement of the catheter 8 relative to the retainer, even when used with a lubricated catheter. The holding effect provided by each of the retention elements, however, does not substantially occlude the lumens of the catheter. The interaction of the protuberances (i.e., the posts and/or projection) only affects the catheter webbing 120 (or like structure) and does not bear against the catheter body. Likewise, the interaction between the shape of the channel 60 and posts 74, 78 restricts movement of the catheter 8 in both axial directions, but does not crimp or kink the catheter body when it is inserted within the channel and about the posts. Further, although the securement protrusions 270 bear against the catheter body, their limited bite does not significantly occlude or penetrate the corresponding catheter lumen. To further prevent occlusion of the catheter lumen, the recessed portions 280 provide space for the catheter 8 to bulge outward, and not inward.

The illustrations of the retainer including some of the above-described forms of the retention elements are merely examples. The retainer can include only one retention element of any given type or possibly several; it can but need not include all types. In addition, any combination of the retention elements in the retainer is also possible.

The present anchoring system thus provides a sterile, tight-gripping, needle- and tape-free way to anchor a medical article to a patient. The retainer thus eliminates use of tape, and if prior protocol required suturing, it also eliminates accidental needle sticks, suture-wound-site infections and scarring. In addition, the retainer can be configured to be used with any of a wide variety of catheters, tubes, wires, and other medical articles. Patient comfort is also enhanced and application time is decreased with the use of the present anchoring system.

As further described below, the retainer 20 can rotate by at least some degree, and preferably by 360 degrees, relative to the anchor pad 12. For this purpose, in the illustrated embodiment, the mounting base 242 is attached to the anchor pad 12 and includes a post 226. A hole 232 is formed in the base 22 of the retainer 20 to receive the post 226.

As best seen in FIGS. 1, 2, 10A, 10B, the mounting post 226 is attached to the anchor pad 12 and the through-hole 232 is formed in the base 22 of the retainer 20. The mounting post 226 and through-hole 232 allow the retainer 20 to pivot relative to the anchor pad 12. In the illustrated embodiment, the retainer 20 can be rotated 360 degrees relative to a central pivot point fixed to the anchor pad 12; however, the degree of rotation also can be confined.

Relative rotation is advantageous to assist the healthcare provider in attaching and detaching the retainer 20 to the catheter. Relative rotation is also advantageous to assist the healthcare provider in adjusting the attached catheter retainer assemblage so that the catheter is less likely to become kinked or snagged on an object. Relative rotation is further advantageous to assist in positioning the catheter in line with the drainage lumen or other object. In addition, the healthcare provider need not precisely align the retainer relative to an axis of the catheter before attaching the pad to the patient's skin. The healthcare provider can coarsely align the anchoring system on the patient, adhere the pad to the patient's skin, and then rotate the retainer to align the channel of the base with the axis of the catheter. The rotatable nature of the retainer thus eases connection and disconnection of the catheter with the retainer.

As best seen in FIGS. 10A, 10B, the illustrated mounting post 226 comprises a pedestal 228 and a cap 230 configured for acceptance into a through-hole 232 formed in the base 22 of the retainer 20. The pedestal 228 is attached to and extends upwardly from the anchor pad 12. The pedestal 228 can have a variety of transverse heights, depending upon the particular application and the particular retainer to which it interacts. For anchoring Foley catheters and for use with some exemplary retainers described herein, the pedestal 228 desirably has a transverse height slightly smaller than that of the base 22 at the location of the hole 232; that is, the height can be about 1-5 mm, and more particularly about 2 mm; however, other heights are also possible. The illustrated pedestal 228 has a generally cylindrical shape, but can be configured in a variety of other shapes, which can match the shape of the hole 232 in the retainer base 22. The diameter of the pedestal 228 is sufficient to perform its structural function of coupling the anchor pad 12 to the base 22 without significantly bending or breaking and desirably has a diameter of about 1 to 5 mm and more particularly a diameter of about 4 mm; however, larger or smaller diameters are also possible. Thus, the diameter of the pedestal 228 is desirably about twice the height of the pedestal 228. The pedestal 228 can be flared at the bottom to form an annular fillet (not shown). The fillet can provide structural strength to the pedestal 226 to resist shear and other forces that can otherwise cause the pedestal to break off from the mounting base 242 or otherwise fail. In other embodiments, the pedestal 228 can form a right angle with the mounting base 242.

The cap 230 extends radially outward from the top portion of the pedestal 228. The cap 230 assists in coupling the anchor pad 12 to the base 22 by inhibiting separation of the pedestal 228 from the base 22, as explained below. The radial diameter of the cap 230 can vary, depending upon the particular application, and desirably is about 1-5 mm, and more particularly a diameter of about 2 mm; however, larger or smaller diameters are also possible. The illustrated cap 230 has a cross sectional shape generally similar to that of the pedestal 228 for ease of manufacture, however, it can be configured in a variety of other cross sectional shapes to generally match the shape of the through-hole 232 in the base, which is described below. The cap 230 desirably extends beyond the circumference of the pedestal 228 to assist in securely coupling the anchor pad 12 to the retainer 20, however, the cap 230 need not circumscribe the entire pedestal 228 and can comprise only a single radial member that extends outwardly from the pedestal 228. The transverse thickness of the cap 230 is sufficient to perform its structural function of coupling the anchor pad 12 to the retainer 20 without significantly bending or breaking and desirably has a thickness of about 0.5 to 2 mm and more particularly a thickness of about 1 mm; however, larger or smaller thicknesses are also possible. A chamfer 234 can be formed on an upper peripheral edge of the cap 230 to assist in the assembly of the mounting post 226, as described below. The illustrated chamfer 234 transversely extends for about one-half the thickness of the cap 230.

The mounting post pedestal 228 desirably has smooth side surfaces to facilitate sliding of the retainer 20 relative to the mounting post 226, such that the mounting post 226 provides a bearing surface for the retainer base 22. The top of the cap 230 additionally is smooth and planar to present a surface that is generally flush with the surface of the base 22 within the channel. It is understood, however, that in the illustrated embodiment the curvilinear configuration of the channel surface of the base 22 and manufacturing variation can result in an imperfectly flush surface between the base and the cap 230. To preserve the integrity of the channel, it will generally be preferred that the cap 230 reside slightly below the channel surface so as to ensure it does not protrude into the channel 60 due to variation in manufacturing or a non-flat channel. The mounting post 226 has a one-piece unitary configuration for ease of manufacture and strength; however, the mounting post 226 can alternatively comprise a plurality of separate components that attach to form the mounting post 226. Although the illustrated mounting post 226 is generally mushroom shaped with a generally flat top, the mounting post 226 can also be generally T-shaped, inversely L-shaped and the like.

The mounting post 226 is desirably formed in unity with a mounting base 242 for structural strength; however, the mounting post 226 and the mounting base 242 can comprise separate components, as noted below. The mounting base 242 provides a larger footprint, relative to that of the mounting post 226, so that the mounting post 226 can be more securely attached to the anchor pad 12 and inhibit unintended separation of the mounting post 226 from the anchor pad 12. For example, if the anchoring system 10 is adhered to the inner thigh of a bedridden patient, movement of the patient can generate forces on the anchoring system 10. Thus, the larger footprint which the mounting base 242 provides, and which the mounting post 226 is preferably in unity with, provides increased securement between the mounting post 226 and anchor pad 12 and enhances the robustness of the anchoring system.

The mounting base 242 is generally planar to match the upper surface 14 of the anchor pad 12. The illustrated plate also has a circular configuration, with the mounting post 226 located at the center of the plate so that the retainer 20 can centrally rotate on the mounting base 242; however, the base can have other shapes as well.

In some embodiments, an upturned lip (not shown) desirably circumscribes the perimeter of the mounting base 242 to form a barrier that inhibits inwardly directed radial forces from shearing or otherwise separating the retainer 20 or mounting post 226 from the mounting base 242. The lip has a transverse height of about 1-5 mm for this purpose. The lip diameter is slightly larger than the lateral width of the retainer 20 (i.e., larger by about 1 mm); however, the lip can alternatively be arranged to radially abut the retainer 20 when the retainer 20 rotates on the mounting base 242, or to provide a radial clearance between the retainer 20 and the lip. When so configured, the lip does not interfere with the interengaging structure (i.e., does not extend transversely above the latching mechanism so as to inhibit the healthcare provider's fingers from depressing the latching mechanism, or abut the retainer so as to partially depress the latching mechanism when the retainer is rotated). The lip additionally does not extend above the bottom of the channel 60 and thus does not present an edge about which the catheter could kink. In the illustrated embodiment, the lip is shorter than the mounting post 226. The lip also does not interfere with the free rotation of the retainer; however, the mounting base 242 and the retainer 20 can include cooperating structure which establishes incremental angular positions of the retainer as it rotates over the mounting base 242. This can be done by providing a plurality of ratchet teeth about the inner side surface of the lip and a cooperating tang formed on the retainer 20. In this manner, the orientation of the retainer 20 on the mounting base 242 can be set until a sufficient force is applied to the retainer to overcome the engagement between the tang and the corresponding ratchet teeth.

In the illustrated embodiment, as best understood from FIGS. 10A, 10B, the base 22 of the retainer 20 has a through-hole 232 sized and configured to recover the post and more preferably to generally match that of the mounting post 226 so that the retainer 20 can rotate relative to the anchor pad 12 about the mounting post 226. The illustrated through-hole 232 extends through the base 22 and has a diameter slightly larger than that of the pedestal 228 and cap 230. The tolerance between the through-hole 232 and the mounting post 226 desirably is about 0.1-0.5 mm and more particularly about 0.1-0.2 mm. Like the mounting post 226, the through-hole 232 has a smooth surface to minimize friction when the retainer is rotated. A chamfer (not shown) can circumscribe the lower portion of the hole 232 to assist in the assembly of the rotatable mounting post 226, as described below.

When assembled, the mounting post 226 is arranged within the through-hole 232 and secured to the anchor pad 12. In particular, the top of the cap 230 is generally flush with the top of the base 22 and the bottom of the pedestal 228 is secured to the anchor pad 12. The mounting base 242 is desirably secured to the upper surface 14 of the anchor pad 12 by a solvent bond adhesive, such as cyanoacylate or other bonding material. One such adhesive is available commercially as Part No. 4693 from the Minnesota Mining and Manufacturing Company (3M). One suitable assembly process, advantageously used when the mounting post 226 and mounting base 242 are formed in unity, involves bonding the bottom of the mounting base 242 to the upper surface 14 of the anchor pad 12 and then urging the cap 230 of the mounting post 226 through the through-hole 232. A chamfer that circumscribes the through-hole 232 and the chamfer 234 that circumscribes the cap 230 can cooperate to allow the cap 230 to deform and advance through the through-hole 232. Another suitable assembly process, advantageously used when the mounting post 226 and mounting base 242 comprise separate components, involves placing the pedestal 228 through the through-hole 232 such that the pedestal 228 extends through while the cap 230 catches on the second diameter 238, then bonding the bottom of the pedestal 228 to the mounting base 242, and then bonding the mounting base 242 to the anchor pad 12. By this configuration, the retainer 20 can rotate 360 degrees relative to the anchor pad 12.

FIGS. 4, 5 shows the top and bottom of the cover 24 having indicia 224, 225 such as a directional arrow, to orient the healthcare provider. The indicia 224 directs the positioning of the retainer 20 with respect to the catheter and the patient. The retainer 20 is desirably arranged so that the arrow points toward the catheter insertion point, and in a direction generally parallel to the longitudinal axis of the catheter 8. Providing indicia 224 on the top of the cover 24 can convey information to the healthcare provider while the retainer 20 is in the closed position. However, this indicia 224 is not visible to the healthcare provider when the retainer 20 is in the open position. Thus, providing indicia 225 on the bottom of the cover 24 can provide information to the healthcare provider when the retainer 20 is in the open position.

To firmly hold the affected catheter portion within the channel, the base 22 and the cover 24 include interengaging structure to couple them together in the closed position. In the illustrated embodiment, as best seen in FIGS. 18-20, a latch mechanism 80 is used to secure the cover 24 to the base 22. The latch mechanism 80 comprises at least one moveable keeper 88, at least one latch post 260, and at least one receptacle 104. The keeper 88 is arranged on the cover 24 while the receptacle 104 is arranged on the base 22; however, these components can be flip-flopped on the base and the cover.

As best seen in FIGS. 4, 8, 18-20, each keeper 88 includes a bar 92 extending toward the base 22 from the second side 34 of the cover 24. Two tangs 94 are formed at a lower end of the bar 92. Desirably, the lower end of the tangs 94 are relatively blunt and smooth to prevent them from puncturing the gloves or skin of a healthcare provider or catching on other materials. An operator lever 98 extends to the side of the bar 92 and includes an enlarged platform or ear at its outer end. The operator lever 98 is angled upwardly from the bar 92 when the cover 24 is in the closed position. In this way, downward force upon the operator lever 98 produces a force component which causes the bar 92 to deflect inwardly, allowing the tangs 94 to disengage from notches 106 on the base 24. The entire keeper 88 desirably is formed with the cover 24 to form a unitary piece.

The base 24 includes a receptacle 104 that receives the bar 92 and the tangs 94. The latch receptacle 104 includes inner notches 106 into which the tangs 94 snap when the cover 24 is in the closed position; however, the tangs can be arranged in the receptacle and the notches be positioned on the bar to accomplish the same effect. The receptacle 104 desirably is formed with the base 22 as a unitary piece.

In the illustrated embodiment there are two tangs 94 and two notches 106 disposed symmetrically from front to back on the retainer. Each notch 106 is arranged to receive one of the keeper tangs 94 when the cover 24 is closed.

An entrance of the receptacle 104 includes chamfer edges. The chamfer edges slope inward toward the center of the receptacle 104 to cause the keeper bars 92 to bend inward when inserting the keepers 88 into the latch receptacle 104.

As best understood from FIGS. 4, 6, the second side 28 of the base 22 also includes a slot 108 to receive a portion of the operator levers 98 and the bar 92 of the keepers 88 when the associated tangs 94 are inserted into the receptacle 104.

In some embodiments, the latch 80 can further comprise one or more latch posts 260 and one or more latch post receiving portions 261, as best depicted in FIGS. 4 and 18-20. As in the illustrated embodiment, the latch post 260 extends from the cover 24 to enter the latch post receiving portion 261 on the base 22. In this embodiment the latch post 260 comprises a substantially close fit with the latch post receiving portion 261. The latch post 260 and receiving portion 261 are located further inside the retainer 20 relative to the bar 92. As shown, the latch post 260 has a taper and a smooth surface, matching the taper and smooth surface of the receiving portion 261, such that the latch post can be easily inserted.

In operation, the cover 24 can swing toward the closed position. The relatively thin strip of material forming the coupling allows the hinge 40 to bend when finger pressure is exerted on the cover 24 to close it. The lower ends of the tangs 94 contact chamfered edges of the latch receptacle 104 when the cover 24 nears its closed position. Continued pressure forces the bar 92 inward to permit the tangs 94 to pass through the receptacle. The slot 108 of the receptacle 104 receives the operator lever 98 as the tangs 94 are pushed further into the receptacle 104. The tangs 94 snap into the notches 106, under the spring force provided by the deflected bar 92 when the cover 22 sits atop the base 24. The interaction between the tangs 94 and the corresponding surfaces of the notches 106 hold the cover 24 in this position. As best seen in FIG. 20, the operator lever 98 extends to the lateral side of the base 24 when the cover 24 is latched.

A healthcare provider presses downward on the operator lever to open the latch mechanism 80. A downwardly force applied to the angled outer surface exerts an inward force component which deflects the bar 92 inward and releases the tangs 94 from the notches 106. The inherent spring force stored in the bent hinge band assists with providing a transverse force that moves the keeper 88 out of the receptacle 104. The healthcare provider can then open the cover 24 and expose the inner grooves 30, 36 of the base 22 and the cover 24.

Certain interengaging elements arranged between interfacing portions of the base 22 and the cover 24 further provide an inherent spring force. As best shown in FIG. 4, the illustrated embodiment shows two sets of interengaging elements, one set arranged near the hinge 40 and one set arranged near the latch mechanism 80. Each set of interengaging elements include a pin 220 that extends from the cover 24 and a receiver 222 that recedes into the base 22. The pin 220 is configured to fit within the recess 222 so that when the cover 24 is closed, the pin 220 extends into the recess 222 to interlock the base 22 and cover 24 together. The transverse length of the pin 220 is desirably sized slightly larger than the transverse depth of the receiver 222 (e.g. about 0.05-0.5 mm). By this arrangement, when the cover 24 is in the closed position, the first side 32 of the cover 24 is offset from (i.e., not in contact with) the first side 26 of the base 22. Thus, the internal spring force stored in the interengaging elements can also provide the suitable transverse force to assist in opening the cover 24. The interengaging elements also serve to interlock the base 22 and the cover 24 in the longitudinal and lateral directions, similar to that of the projection 81 and receptacle 79 of the previous embodiment.

Under the deflection of both opening and closing the retainer 20, the latch post and receiving portion 260, 261 act to constrain this deflection to the bar 92 and prevent similar deflection in the cover 24 or the base 22. Absent the latch post and receiving portion 260, 261 the deflecting force could cause the cover 24 and base 22 to bow away from each other, potentially causing undesirable pinching or kinking of the catheter 8 upon closing of the retainer 20. A latch post and receiving portion 260, 261 that substantially match each other can act to resist bowing of the cover 24 relative to the base 22. Thus, the latch post and receiving portion 260, 261 can provide structural support to the latch 80. As best shown in FIG. 19, when the latch 80 is in transition between open and closed positions the latch post 260 deflects backward to push against the latch post receiving portion 261. Absent this structure, the deflecting force could travel the length of the cover 22.

The releasable engagement between the cover 24 and the base 22 allows the same retainer 20 to be used even when opened and closed multiple times. This allows for repeated attachment and reattachment of the catheter to the anchoring system 10. In addition, the hinged connection connecting the cover 24 to the base 22 ensures that the cover 24 will not be lost or misplaced when the catheter is detached from the anchoring system 10. The healthcare provider wastes no time in searching for a cover, nor in orienting the cover prior to latching.

The catheter 8 can comprise a number of materials, including silicone, latex, plastics, rubber, polypropylene, thermoplastics, or other materials. In a preferred embodiment a silicone catheter is used. The retention elements (e.g. protrusions 270, channel 60, posts 74, 78, etc.) can be included, shaped, and positioned according to the material used. For example, a catheter 8 comprising a material with stronger frictional forces may require fewer and/or weaker retention elements on the retainer 20 to hold it in place. A catheter 8 comprising a material, shape, or size that easily kinks may require relatively broader and more finely adapted retention elements on the retainer 20 to sufficiently hold it in place and prevent kinks.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure and the claims that follow.

What is claimed is:

1. A catheter securement device, comprising:
   a catheter;
   an anchor pad having an adhesive layer disposed on at least a portion thereof;
   a retainer including a channel configured to retain a portion of the catheter, the portion of the catheter comprising a branched section, the retainer comprising a first portion hingedly attached to a second portion, moveable between an open position and a closed position, the first portion including two posts and the second portion including two posts, the first portion posts configured to engage the second portion posts so as to form a portion of a distal surface of the retainer when the retainer is in the closed position; and
   a latching mechanism configured to releasably secure the first and second portion in the closed position, the latching mechanism including:
   at least one moveable keeper;
   an operator lever; and
   at least one latch post disposed between a of the channel wall and the at least one moveable keeper, and designed to engage an outer surface of the wall to prevent over-deflection of the at least one moveable keeper toward the portion of the catheter when a force is applied to the operator lever.

2. The catheter securement device according to claim 1, wherein the second portion posts are configured to engage the portion of the catheter so as to restrict movement of the catheter in at least a longitudinal direction.

3. The catheter securement device according to claim 1, wherein the retainer is rotatably coupled to the anchor pad.

4. The catheter securement device according to claim 1, wherein the posts on the first portion and the posts on the second portion define three openings in the distal surface of the retainer when the retainer is in the closed position.

5. The catheter securement device according to claim 1, wherein the retainer is composed of polypropylene.

6. The catheter securement device according to claim 1, wherein the first and second portions include a plurality of protrusions.

7. The catheter securement device according to claim 6, wherein the plurality of protrusions are positioned opposite one another.

8. The catheter securement device according to claim 6, wherein the plurality of protrusions inhibit longitudinal movement of the catheter.

9. The retainer according to claim 1, further comprising directional marks visible to a user when the retainer is in both the open and closed positions.

10. The retainer according to claim 9, wherein the directional marks are arrows.

11. The retainer according to claim 9, wherein the directional marks are on both a top and bottom of the retainer.

12. The retainer according to claim 1, wherein the at least one latch post prevents impingement of the portion of the catheter when a force is applied to the operator lever.

13. The retainer according to claim 1, wherein engagement between the at least one latch post and the outer surface of the wall resists bowing of at least one of the first and second portions of the retainer.

14. The retainer according to claim 1, wherein engagement between the at least one latch post and the outer surface of the wall resists bowing of at least one of the first and second portions of the retainer when a force is applied to the operator lever.

15. The retainer according to claim 1, wherein the at least one latch post is designed to prevent a deflecting force from traveling along a length of at least one of the first and second portions of the retainer.

* * * * *